United States Patent
Heckel et al.

(10) Patent No.: US 9,981,954 B2
(45) Date of Patent: May 29, 2018

(54) 2-(PYRAZIN-2-YLCARBONYLAMINOMETHYL) BENZIMIDAZOLIUM COMPOUNDS AS EPITHELIAL SODIUM CHANNEL INHIBITORS

(71) Applicant: Boehringer Ingelheim International GmbH, Ingelheim am Rhein (DE)

(72) Inventors: Armin Heckel, Biberach an der Riss (DE); Sara Frattini, Castelleone (IT); Joerg Kley, Mittelbiberach (DE)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 0 days. days.

(21) Appl. No.: 15/542,896

(22) PCT Filed: Jan. 7, 2016

(86) PCT No.: PCT/EP2016/050169
§ 371 (c)(1),
(2) Date: Jul. 11, 2017

(87) PCT Pub. No.: WO2016/113168
PCT Pub. Date: Jul. 21, 2016

(65) Prior Publication Data
US 2018/0002314 A1 Jan. 4, 2018

(30) Foreign Application Priority Data
Jan. 12, 2015 (EP) .................................. 15150833

(51) Int. Cl.
| | | |
|---|---|---|
| *C07D 403/12* | (2006.01) | |
| *A61K 31/497* | (2006.01) | |
| *A61K 31/5377* | (2006.01) | |
| *A61K 31/551* | (2006.01) | |
| *A61K 31/675* | (2006.01) | |
| *A61K 45/06* | (2006.01) | |
| *C07C 53/18* | (2006.01) | |
| *C07D 401/14* | (2006.01) | |
| *C07D 405/14* | (2006.01) | |
| *C07F 9/6509* | (2006.01) | |

(52) U.S. Cl.
CPC .......... *C07D 403/12* (2013.01); *A61K 31/497* (2013.01); *A61K 31/5377* (2013.01); *A61K 31/551* (2013.01); *A61K 31/675* (2013.01); *A61K 45/06* (2013.01); *C07C 53/18* (2013.01); *C07D 401/14* (2013.01); *C07D 405/14* (2013.01); *C07F 9/650994* (2013.01)

(58) Field of Classification Search
CPC .. C07D 403/12; C07D 401/14; C07D 405/14; C07C 53/18; A61K 31/497; A61K 31/5377; A61K 31/551; A61K 31/675; A61K 45/06
USPC ........................................................ 514/80
See application file for complete search history.

(56) References Cited

FOREIGN PATENT DOCUMENTS

WO     11079087 A1    6/2011

OTHER PUBLICATIONS

Schoenberger et al., "Novel small molecule epithelial sodium channel inhibitors as potential therapeutics in cystic fibrosis—a patent evaluation", Expert Opinion on Therapeutic Patents, Informa Healthcare, 2013, vol. 23, No. 10, pp. 1383-1389.
International Search Report and Written Opinion for corresponding application PCT/EP2016/050169, dated May 30, 2016.

*Primary Examiner* — Kahsay Habte
(74) *Attorney, Agent, or Firm* — Marc Began; Philip I. Datlow

(57) ABSTRACT

The present invention relates to compounds of formula (I) or the tautomers or pharmacologically acceptable acid addition salts thereof, characterized by a topological polar surface area value (TPSA) of at least 145, wherein $R^1$, $R^2$, $R^3$, $R^4$, X, and $Z^-$ have one of the meanings as defined in the specification, to the use of compounds of formula (I) as medicaments, to pharmaceutical compositions comprising at least one compound of formula (I), as well as to medicament combinations containing one or more compounds of formula (I). The compounds are ENaC inhibitors useful for the treatment of respiratory diseases and allergic diseases of the airways.

16 Claims, No Drawings

2-(PYRAZIN-2-YLCARBONYLAMINOMETHYL) BENZIMIDAZOLIUM COMPOUNDS AS EPITHELIAL SODIUM CHANNEL INHIBITORS

FIELD OF THE INVENTION

The present invention relates to compounds of formula (I) or the tautomers or pharmacologically acceptable acid addition salts thereof,

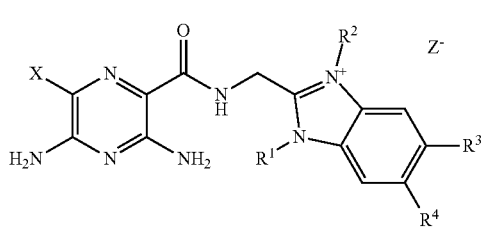

characterized by a topological polar surface area value (TPSA) of at least 145, wherein $R^1$, $R^2$, $R^3$, $R^4$, X, and $Z^-$ have one of the meanings as defined in the specification, to the use of compounds of formula (I) as a medicament, to pharmaceutical composition comprising at least one compound of formula (I), as well as to medicament combinations containing one or more compounds of formula (I).

BACKGROUND TO THE INVENTION

WO2011079087 discloses compounds of similar structure showing ENaC (Epithelial Sodium Channel) inhibitor activity.

The problem of the present invention is to prepare new compounds which may be used therapeutically for the treatment of pathophysiological processes treatable by the blockade of an epithelial sodium channel, particularly for the treatment of the lungs and airways. The new compounds of the present invention exhibit a longer lasting activity in topical lung treatment. The new compounds of the present invention further exhibit a reduced permeability being beneficial for topical lung treatment.

DETAILED DESCRIPTION OF THE INVENTION

The present invention relates to compounds of formula (I), or to the tautomers or pharmacologically acceptable acid addition salts thereof,

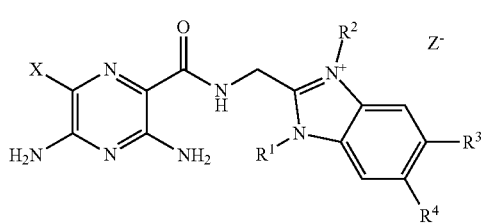

wherein
$R^3$ is H or $C_1$-$C_4$-alkoxy;
$R^4$ is H or $C_1$-$C_4$-alkoxy;
X is Cl or Br; and $Z^-$ is chloride, bromide, iodide, hydroxide, hydrogensulfate, sulfate, nitrate, phosphate, formate, acetate, trifluoroacetate, fumarate, citrate, tartrate, oxalate, succinate, mandelate, methanesulfonate or p-toluenesulfonate;
wherein at least one of $R^1$ and $R^2$ is independently selected from a group of formula (A),

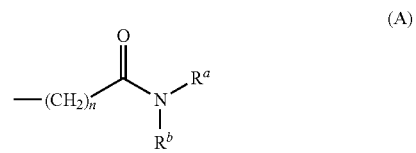

wherein
n is 1, 2 or 3, and
$R^a$ and $R^b$ are independently selected from H, $C_1$-$C_4$-alkyl, wherein $C_1$-$C_4$-alkyl in the aforementioned moiety may carry a substituent selected from amino, $C_1$-$C_4$-alkylamino, di($C_1$-$C_4$-alkyl)amino, hydroxy, $C_1$-$C_4$-alkoxy, $C_1$-$C_4$-alkoxycarbonylamino-, and $C_1$-$C_4$-alkoxycarbonyl($C_1$-$C_4$-alkyl)amino-, or a 5- to 7-membered heterocycle containing 1 or 2 heteroatoms selected from O and N, wherein the 5- to 7-membered heterocycle may carry one substituent selected from $C_1$-$C_4$-alkyl and $C_1$-$C_4$-alkoxycarbonyl-;
or wherein $R^a$ and $R^b$ together with the nitrogen they are attached to form a 5- to 7-membered heterocycle containing 1 or 2 heteroatoms selected from O and N, wherein the 5- to 7-membered heterocyclyl may carry one substituent selected from $C_1$-$C_4$-alkyl, amino, $C_1$-$C_4$-alkylamino, di($C_1$-$C_4$-alkyl)amino, hydroxy, $C_1$-$C_4$-alkoxy, and $C_1$-$C_4$-alkoxycarbonyl-;
and/or wherein at least one of $R^1$ and $R^2$ is independently selected from a group of formula (B),

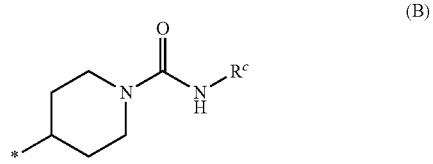

wherein $R^c$ is selected from $C_1$-$C_3$-alkyl, $C_1$-$C_2$-alkoxy-$C_2$-$C_3$-alkyl-, hydroxy-$C_2$-$C_3$-alkyl-, and amino-$C_2$-$C_3$-alkyl-, and wherein * denotes the point of attachment;
and/or wherein at least one of $R^1$ and $R^2$ is independently selected from

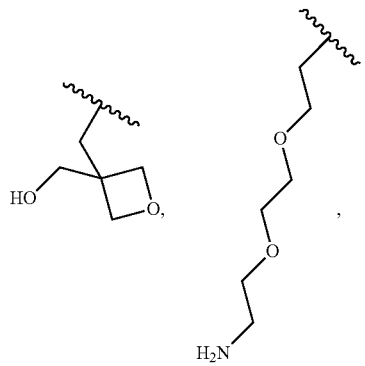

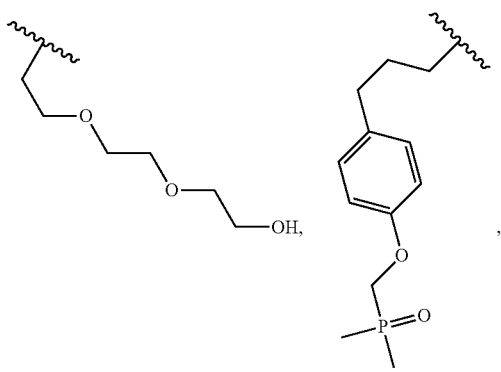

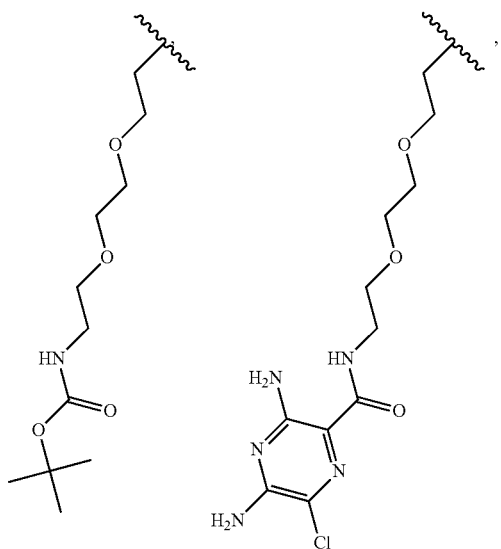

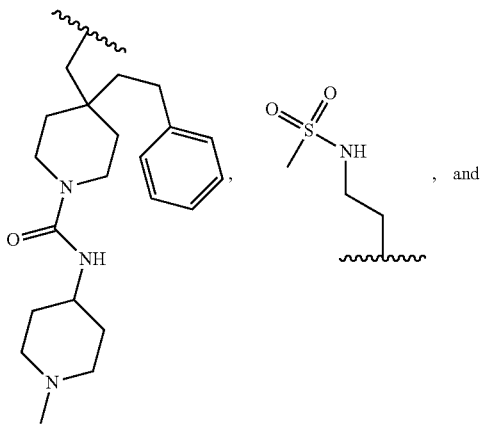

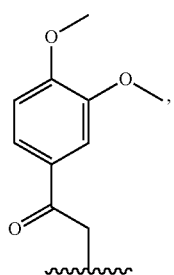

wherein denotes the point of attachment; and
the remaining substituent $R^1$ or $R^2$ may additionally be selected from $C_1$-$C_3$-alkyl, ω-fluoro-$C_2$-$C_3$-alkyl, 2-propenyl, dimethylaminocarbonylmethyl, and dimethylaminocarbonylpropyl;
provided that if one of the substituents $R^1$ or $R^2$ is selected from $C_1$-$C_3$-alkyl the other substituent $R^1$ or $R^2$ is different from —(CH$_2$—CH$_2$—O)$_3$H.

The compounds of formula (I) according to the present invention are characterized by a topological polar surface area value (TPSA) of at least 145. The term "topological polar surface area" as used herein refers to a value calculated as described in Ertl P. et al., J. Med. Chem, 43 (2000), 3714-3717. Suitable compounds of formula (I) will usually have a TPSA value in the range of from 145 to 250.

The compounds of formula (I) or the pharmaceutically acceptable salts thereof as defined herein are particularly suitable for the treatment of pathophysiological processes treatable by the blockade of an epithelial sodium channel, particularly for the treatment of the lungs and airways.

Accordingly the present invention further relates to compounds of formula (I) as defined herein or the tautomers or pharmacologically acceptable acid addition salts thereof for use as a medicament.

The present invention further relates to compounds of formula (I) as defined herein or the tautomers or pharmacologically acceptable acid addition salts thereof for use in the treatment of a disease selected from among respiratory diseases or complaints and allergic diseases of the airways.

The present invention further relates to compounds of formula (I) as defined herein or the tautomers or pharmacologically acceptable acid addition salts thereof for use in the treatment of a disease selected from among chronic bronchitis, acute bronchitis, bronchitis caused by bacterial or viral infection or fungi or helminths, allergic bronchitis, toxic bronchitis, chronic obstructive bronchitis (COPD), asthma (intrinsic or allergic), pediatric asthma, bronchiectasis, allergic alveolitis, allergic or non-allergic rhinitis, chronic sinusitis, cystic fibrosis, mucoviscidosis, alpha-1-antitrypsin deficiency, cough, pulmonary emphysema, interstitial lung diseases, alveolitis, hyperreactive airways, nasal polyps, pulmonary oedema, pneumonitis of different origins, and dry eyes.

The present invention further relates to pharmaceutical compositions comprising at least one compound of formula (I) as defined herein or pharmacologically acceptable acid addition salts thereof and a pharmaceutically acceptable carrier.

The present invention further relates to medicament combinations containing besides one or more compound of formula (I) as defined herein or the tautomers or pharmacologically acceptable acid addition salts thereof, as further active substances, one or more compound selected from among the categories of further ENaC inhibitors, betamimetics, anticholinergics, corticosteroids, PDE4-inhibitors, LTD4-antagonists, EGFR-inhibitors, dopamine agonists, H1 antihistamines, PAF-antagonists, MAP-kinase inhibitors, MPR4-Inhibitors, iNOS-Inhibitors, SYK-Inhibitors, corrections of the cystic fibrosis transmembrane regulator (CFTR) and CFTR potentiators or double or triple combinations thereof.

Terms and Definitions

Terms not specifically defined herein should be given the meanings that would be given to them by one of skill in the art in light of the disclosure and the context. As used in the specification, however, unless specified to the contrary, the following terms have the meaning indicated and the following conventions are adhered to.

In the groups, radicals, or moieties defined below, the number of carbon atoms is often specified preceding the group, for example, $C_{1-6}$-alkyl means an alkyl group or radical having 1 to 6 carbon atoms.

In general in single groups like HO, $H_2N$, OS, $O_2S$, NC (cyano), HOOC, $F_3C$ or the like, the skilled artisan can see the radical attachment point(s) to the molecule from the free valences of the group itself. For combined groups comprising two or more subgroups, the terminal term indicates the radical attachment point, for example, the substituent "aryl-$C_{1-3}$-alkyl" means an aryl group which is bound to a $C_{1-3}$-alkyl-group, the latter of which is bound to the core or to the group to which the substituent is attached.

In case a compound of the present invention is depicted in form of a chemical name and as a formula in case of any discrepancy the formula shall prevail.

Many of the following terms may be used repeatedly in the definition of a formula or group and in each case have one of the meanings given above, independently of one another.

Unless specifically indicated, according to the invention a given chemical formula or name shall encompass tautomers and all stereo, optical and geometrical isomers (e.g. enantiomers, diastereomers, E/Z isomers etc.) and racemates thereof as well as mixtures in different proportions of the separate enantiomers, mixtures of diastereomers, or mixtures of any of the foregoing forms where such isomers and enantiomers exist, as well as salts, including pharmaceutically acceptable salts thereof and solvates thereof such as for instance hydrates including solvates of the free compounds or solvates of a salt of the compound.

The term "substituted" as used herein, means that any one or more hydrogens on the designated atom is replaced with a selection from the indicated group, provided that the designated atom's normal valence is not exceeded, and that the substitution results in a stable compound.

By the term "optionally substituted" is meant within the scope of the invention the above-mentioned group, optionally substituted by a lower-molecular group. Examples of lower-molecular groups regarded as chemically meaningful are groups consisting of 1-200 atoms. Preferably such groups have no negative effect on the pharmacological efficacy of the compounds. For example the groups may comprise: Straight-chain or branched carbon chains, optionally interrupted by heteroatoms, optionally substituted by rings, heteroatoms or other common functional groups.

The expressions "prevention", "prophylaxis", "prophylactic treatment" or "preventive treatment" used herein should be understood synonymous and in the sense that the risk to develop a condition mentioned hereinbefore is reduced, especially in a patient having elevated risk for said conditions or a corresponding anamnesis, e.g. elevated risk of developing metabolic disorder such as diabetes or obesity or another disorder mentioned herein. Thus the expression "prevention of a disease" as used herein means the management and care of an individual at risk of developing the disease prior to the clinical onset of the disease. The purpose of prevention is to combat the development of the disease, condition or disorder, and includes the administration of the active compounds to prevent or delay the onset of the symptoms or complications and to prevent or delay the development of related diseases, conditions or disorders. Success of said preventive treatment is reflected statistically by reduced incidence of said condition within a patient population at risk for this condition in comparison to an equivalent patient population without preventive treatment.

The expression "treatment" or "therapy" means therapeutic treatment of patients having already developed one or more of said conditions in manifest, acute or chronic form, including symptomatic treatment in order to relieve symptoms of the specific indication or causal treatment in order to reverse or partially reverse the condition or to delay the progression of the indication as far as this may be possible, depending on the condition and the severity thereof. Thus the expression "treatment of a disease" as used herein means the management and care of a patient having developed the disease, condition or disorder. The purpose of treatment is to combat the disease, condition or disorder. Treatment includes the administration of the active compounds to eliminate or control the disease, condition or disorder as well as to alleviate the symptoms or complications associated with the disease, condition or disorder.

The phrase "pharmacologically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, and commensurate with a reasonable benefit/risk ratio.

As used herein, "pharmacologically acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. For example, such salts include salts from ammonia, L-arginine, betaine, benethamine, benzathine, calcium hydroxide, choline, deanol, diethanolamine (2,2'-iminobis(ethanol)), diethylamine, 2-(diethylamino)-ethanol, 2-aminoethanol, ethylenediamine, N-ethyl-glucamine, hydrabamine, 1H-imidazole, lysine, magnesium hydroxide, 4-(2-hydroxyethyl)-morpholine, piperazine, potassium hydroxide, 1-(2-hydroxyethyl)pyrrolidine, sodium hydroxide, triethanolamine (2,2',2"-nitrilotris(ethanol)), tromethamine, zinc hydroxide, acetic acid, 2.2-dichloro-acetic acid, adipic acid, alginic acid, ascorbic acid, L-aspartic acid, benzenesulfonic acid, benzoic acid, 2,5-dihydroxybenzoic acid, 4-acetamido-benzoic acid, (+)-camphoric acid, (+)-camphor-10-sulfonic acid, carbonic acid, cinnamic acid, citric acid, cyclamic acid, decanoic acid, dodecylsulfuric acid, ethane-1,2-disulfonic acid, ethanesulfonic acid, 2-hydroxy-ethanesulfonic acid, ethylenediaminetetraacetic acid, formic acid, fumaric acid, galactaric acid, gentisic acid, D-glucoheptonic acid, D-gluconic acid, D-glucuronic acid, glutamic acid, glutaric acid, 2-oxo-glutaric acid, glycerophosphoric acid, glycine, glycolic acid, hexanoic acid, hippuric acid, hydrobromic acid, hydrochloric acid, isobutyric acid, DL-lactic acid, lactobionic acid, lauric acid, lysine, maleic acid, (−)-L-malic acid, malonic acid, DL-mandelic acid, methanesulfonic acid, galactaric acid, naphthalene-1,5-disulfonic acid, naphthalene-2-sulfonic acid, 1-hydroxy-2-naphthoic acid, nicotinic acid, nitric acid, octanoic acid, oleic acid, orotic acid, oxalic acid, palmitic acid, pamoic acid (embonic acid), phosphoric acid, propionic acid, (−)-L-pyroglutamic acid, salicylic acid, 4-amino-salicylic acid, sebacic acid, stearic acid, succinic acid, sulfuric acid, tannic acid, (+)-L-tartaric acid, thiocyanic acid, p-toluenesulfonic acid and undecylenic acid. Further pharmaceutically acceptable salts can be formed with cations from metals like aluminium, calcium, lithium, magnesium, potassium, sodium, zinc and the like. (also see Pharmaceutical salts, Berge, S. M. et al., J. Pharm. Sci., (1977), 66, 1-19).

The pharmacologically acceptable salt of the present invention can be synthesized from the parent compound which contains a cationic group and optionally an additional basic or acidic moiety by conventional chemical methods. Generally, such salts can be prepared by reacting other salt forms of these compounds with a sufficient amount of the appropriate base or acid in water or in an organic diluent like ether, ethyl acetate, ethanol, isopropanol, or acetonitrile, or a mixture thereof. Moreover, counterions can generally be exchanged by ion exchange chromatography.

Salts of other acids than those mentioned above which for example are useful for purifying or isolating the compounds of the present invention (e.g. trifluoro acetate salts) also comprise a part of the invention.

The term "heterocyclyl" or "heterocycle" means a saturated or unsaturated mono- or polycyclic-ring systems including aromatic ring system containing one or more heteroatoms selected from N, O or $S(O)_r$, wherein r=0, 1 or 2, consisting of 3 to 14 ring atoms wherein none of the heteroatoms is part of the aromatic ring. The term "heterocycle" is intended to include all possible isomeric forms.

Thus, the term "5- to 7-membered heterocycle containing 1 or 2 heteroatoms selected from O and N" includes the following exemplary structures which are not depicted as radicals as each form may be attached through a covalent bond to any atom so long as appropriate valences are maintained:

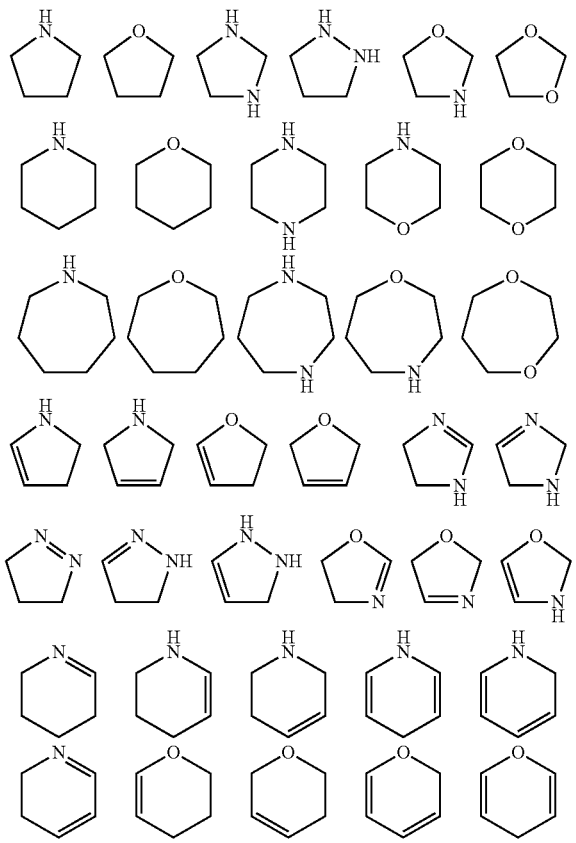
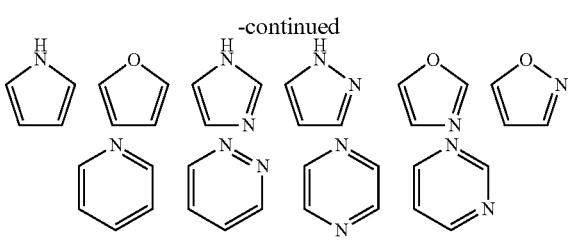

The term "$C_{1\text{-}n}$-alkyl", wherein n is an integer from 2 to n, either alone or in combination with another radical denotes an acyclic, saturated, branched or linear hydrocarbon radical with 1 to n C atoms. For example the term $C_{1\text{-}5}$-alkyl embraces the radicals $H_3C$—, $H_3C$—$CH_2$—, $H_3C$—$CH_2$—$CH_2$—, $H_3C$—$CH(CH_3)$—, $H_3C$—$CH_2$—$CH_2$—$CH_2$—, $H_3C$—$CH_2$—$CH(CH_3)$—, $H_3C$—$CH(CH_3)$—$CH_2$—, $H_3C$—$C(CH_3)_2$—, $H_3C$—$CH_2$—$CH_2$—$CH_2$—$CH_2$—, $H_3C$—$CH_2$—$CH_2$—$CH(CH_3)$—, $H_3C$—$CH_2$—$CH(CH_3)$—$CH_2$—, $H_3C$—$CH(CH_3)$—$CH_2$—$CH_2$—, $H_3C$—$CH_2$—$C(CH_3)_2$—, $H_3C$—$C(CH_3)_2$—$CH_2$—, $H_3C$—$CH(CH_3)$—$CH(CH_3)$— and $H_3C$—$CH_2$—$CH(CH_2CH_3)$—.

The term "$C_{1\text{-}6}$-alkoxy" (including those which are part of other groups) denotes branched and unbranched alkoxy groups with 1 to 6 carbon atoms and by the term "$C_{1\text{-}4}$-alkoxy" are meant branched and unbranched alkoxy groups with 1 to 4 carbon atoms. Alkoxy groups with 1 to 4 carbon atoms are preferred. Examples include: methoxy, ethoxy, propoxy, butoxy or pentoxy. The abbreviations OMe, OEt, OPr, etc. may optionally be used for the above-mentioned groups. Unless stated otherwise, the definitions propoxy, butoxy and pentoxy include all the possible isomeric forms of the respective groups. Thus for example propoxy includes n-propoxy and iso-propoxy, butoxy includes iso-butoxy, sec-butoxy and tert-butoxy etc.

In all cases of contradictions between structure and their naming, structure shall prevail.

Preferred Embodiments

One particular embodiment of the present invention relates to compounds of formula (I) as defined herein or to the tautomers or pharmacologically acceptable acid addition salts thereof, wherein $R^3$ is H or —$OCH_3$.

Another particular embodiment of the present invention relates to compounds of formula (I) as defined herein or to the tautomers or pharmacologically acceptable acid addition salts thereof, wherein $R^4$ is H or —$OCH_3$.

The present invention relates to compounds of formula (I) as defined herein or to the tautomers or pharmacologically acceptable acid addition salts thereof, wherein $Z^-$ is chloride, bromide, iodide, hydroxide, hydrogensulfate, sulfate, nitrate, phosphate, formate, acetate, trifluoroacetate, fumarate, citrate, tartrate, oxalate, succinate, mandelate, methanesulfonate or p-toluenesulfonate. If $Z^-$ is selected from anions carrying more than one negative charge, such as fumarate, citrate, tartrate, oxalate, or succinate, $Z^-$ may represent the monovalent equivalent part of such an anion. Alternatively, $Z^-$ may represent the respective partially protonated form, such as hydrogenfumarate, hydrogencitrate, dihydrogencitrate, hydrogentartrate, etc.

One particular embodiment of the present invention relates to compounds of formula (I) as defined herein or to the tautomers or pharmacologically acceptable acid addition salts thereof, wherein $Z^-$ is chloride, bromide, formate, or trifluoroacetate.

Another particular embodiment of the present invention relates to compounds of formula (I) as defined herein or to the tautomers or pharmacologically acceptable acid addition salts thereof, wherein at least one of $R^1$ and $R^2$ is independently selected from a group of formula (A).

Preferred are compounds of formula (I) or the tautomers or pharmacologically acceptable acid addition salts thereof, carrying a group of formula (A) wherein n is 1. Suitable examples of such groups of formula (A) are

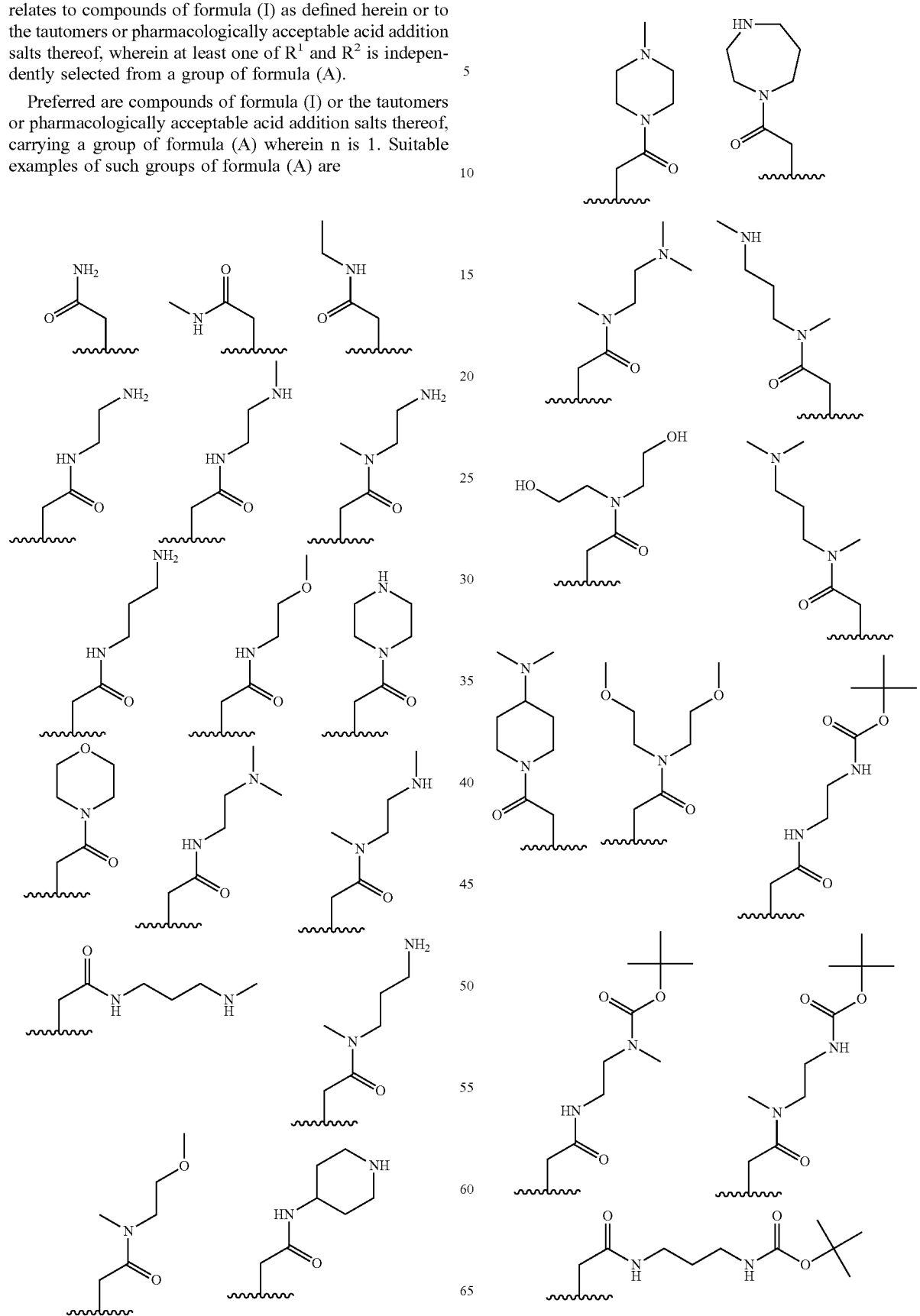

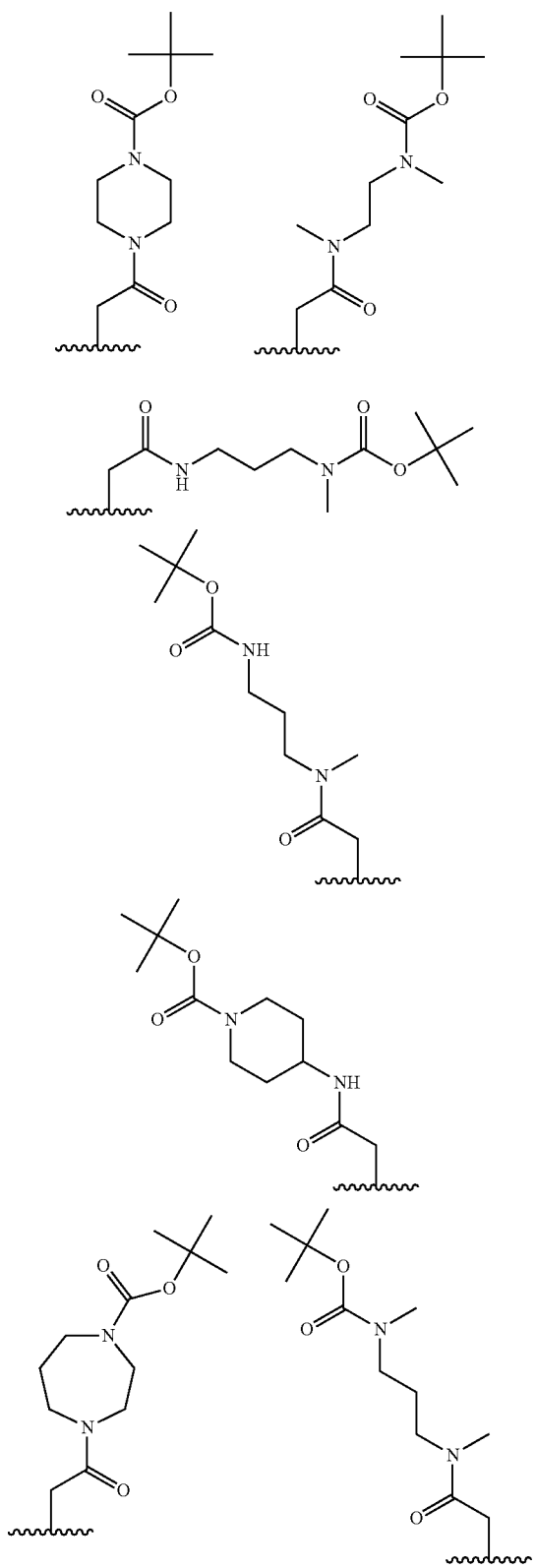
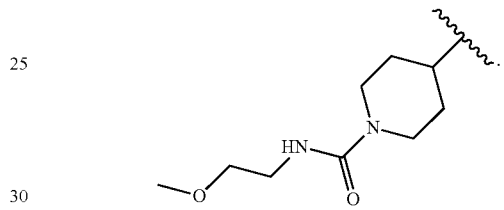

Preferred as well are compounds of formula (I), or the tautomers or pharmacologically acceptable acid addition salts thereof, carrying a group of formula (A) wherein n is 3. Suitable examples of such groups of formula (A) are Another particular embodiment of the present invention relates to compounds of formula (I) as defined herein or to the tautomers or pharmacologically acceptable acid addition salts thereof, wherein at least one of $R^1$ and $R^2$ is independently selected from a group of formula (B). One suitable example of such a group of formula (B) is In the above embodiments of the present invention the compounds of formula (I) as defined herein or to to the tautomers or pharmacologically acceptable acid addition salts thereof, the remaining substituent $R^1$ or $R^2$ is preferably selected from ethyl, 2-fluoroethyl, 2-propenyl, and dimethylaminocarbonylmethyl.

Any substituent defined above may be combined with any other substituent defined above. Particularly preferred are compounds of formula (I) or the pharmaceutically acceptable salts thereof wherein at least 2, 3, 4, 5, or 6 of the substituents defined herein have one of the particular or preferred meaning as defined herein.

Preparation

The following methods are suitable for preparing compounds of general formula (I).

The compounds according to the invention may be obtained using methods of synthesis which are known to the one skilled in the art and described in the literature of organic synthesis. General methods for functional group protection and deprotection are described e.g. in: Greene, T. W. and Wuts, P. G. M. (eds.): Protective Groups in Organic Synthesis, third edition 1999; John Wiley and Sons, Inc. Preferably the compounds are obtained analogously to the methods of preparation explained more fully hereinafter, in particular as described in the experimental section.

Compounds of general formula (I) can be prepared by standard amidation procedures from amines of general formula (II) and the appropriate 3,5-diaminopyrazine-2-carboxylic acid applying e.g. the coupling reagent HATU. Amines (II) can be prepared from N-protected precursors of general formula (III) by standard deprotection procedures. Suitable protecting groups in (III) are e.g. BOC (wherein RPG denotes —NHPG with PG denoting tertBu-OC(O)—) and phthaloyl (wherein RPG denotes phthalimide). Compounds (III) can be prepared by alkylation of benzimidazoles of general formula (IIIa) applying alkylating agents $R^1$-LG. The leaving group LG can be e.g. Br or I.

Alternatively, compounds of general formula (I) can be prepared by alkylation of benzimidazoles of general formula (Ia) applying alkylating agents $R^1$-LG. The leaving group LG can be e.g. Br or I. Compounds of general formula (Ia) can be prepared by standard amidation procedures from amines of general formula (IIa) and the appropriate 3,5-diaminopyrazine-2-carboxylic acid applying e.g. the coupling reagent HATU. Amines (IIa) can be prepared from N-protected precursors of general formula (IIIa) by standard deprotection procedures. Suitable protecting groups in (IIIa) are e.g. BOC (wherein RPG denotes —NHPG with PG denoting tert-BuOC(O)—) and phthaloyl (wherein RPG denotes phthalimide).

Benzimidazoles (IIIa) can be prepared from phenylenediamines (IV) in a two step procedure comprising (i) amidation with N-protected glycine using e.g. the coupling reagent TBTU and (ii) ring closure under acid catalysis, e.g. in glacial acetic acid at elevated temperature.

Phenylenediamines can be prepared from the respective nitroanilines (V) by standard nitro reduction conditions (e.g. catalytic hydrogenation using raney-nickel as a catalyst).

Compounds (V) can be prepared from derivatives (VI) by nucleophilic substitution of the leaving group LG (e.g. F or Cl) with a primary amine $R^2$—$NH_2$ as nucleophile. Alternatively, compounds (V) can be accessed from nitroanilines (Va) by either alkylation (using an alkylating agent $R^2$-LG) or reductive amination (using an appropriate aldehyde) of the aromatic amino group.

Compounds (I), (Ia), (III), (IIIa) and (V) can be modified using methods of synthesis which are known to one skilled in the art and described in the literature of organic synthesis, preferably by functional group protection or deprotection steps, esterifications, amidation, hydrogenations, or 1,3-dipolar cycloadditions. Thereby, before such a modification, the structures of $R^1$, $R^2$, $R^3$, and $R^4$ may be beyond of what is claimed hereinafter.

The skilled person will appreciate that within these general synthesis schemes, the substituents $R^1$ and $R^2$ can in principle be interchanged, meaning that $R^2$ instead of $R^1$ can be introduced in the late alkylation step applying an alkylating agent $R^2$-LG.

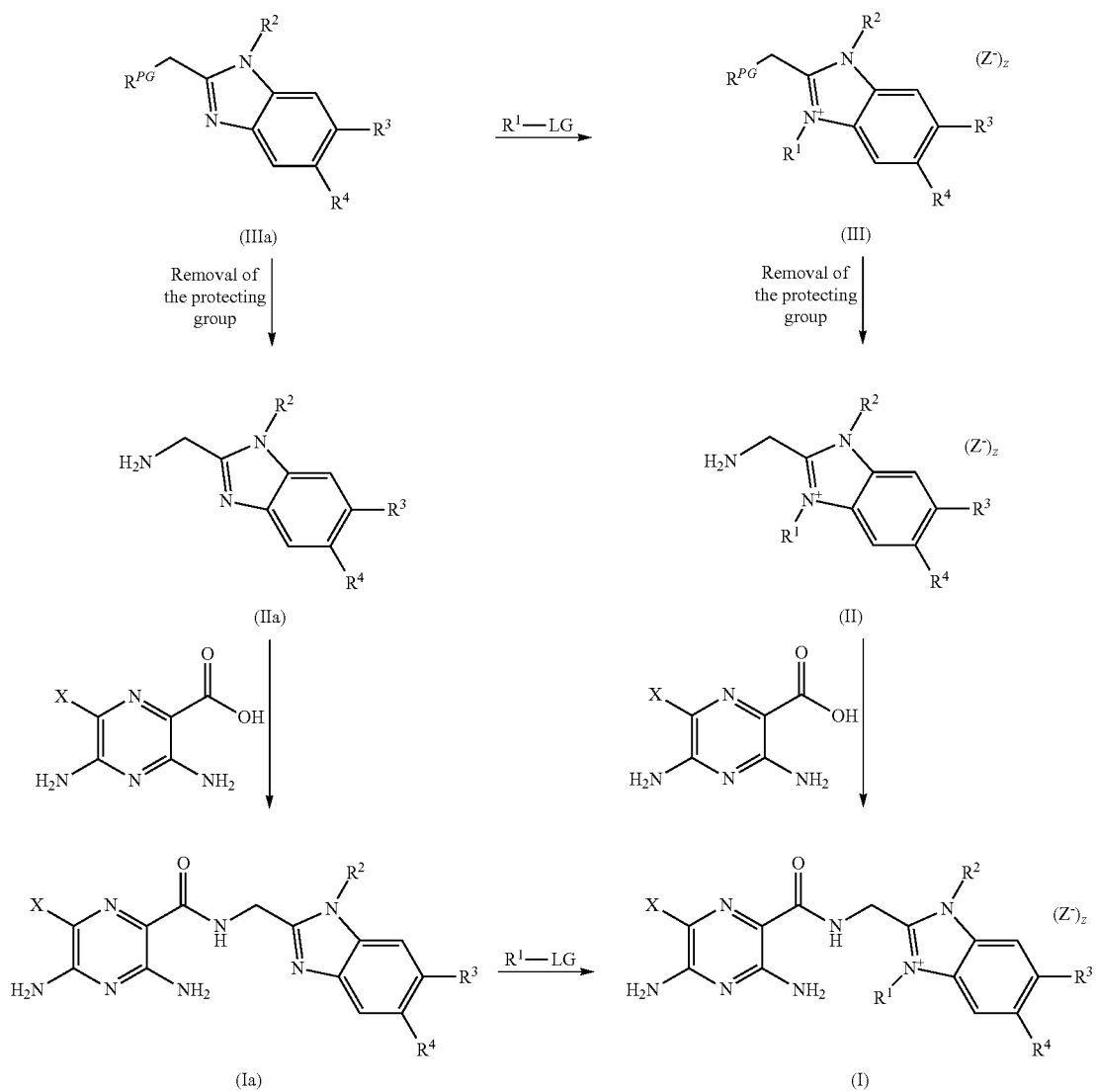

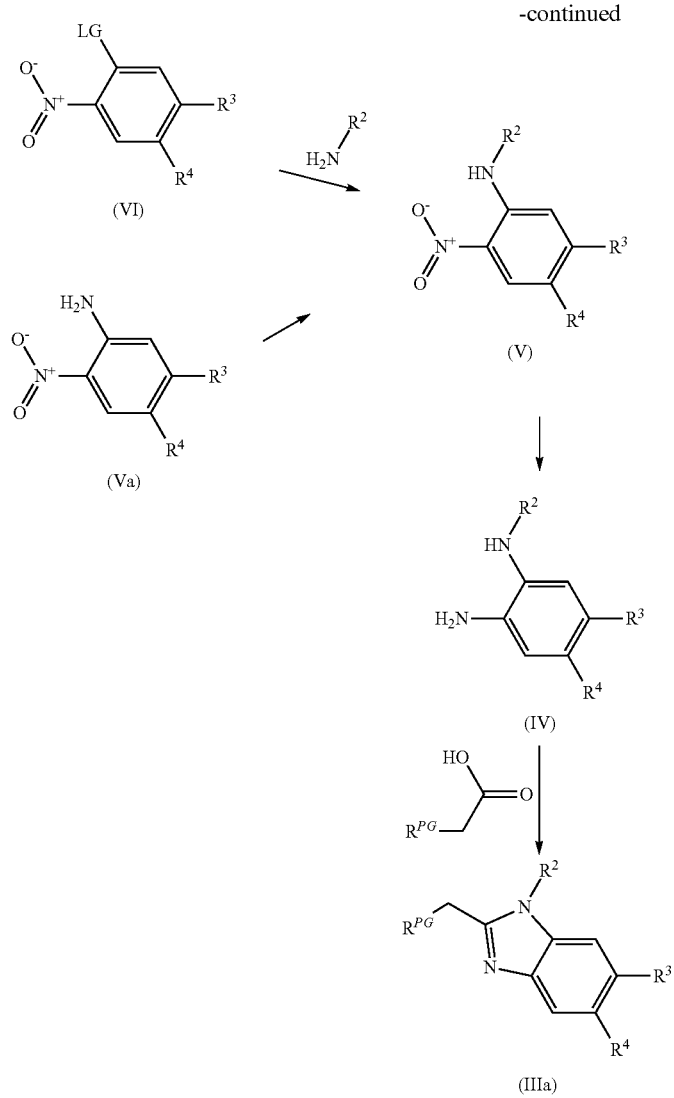

Compounds of formula (I), as defined hereinbefore, are salts containing an anion $Z^-$. These anions $Z^-$ may be derived from synthesis or purification or changed from one anionic species to another suitable anionic species by methods known to those skilled in the art. Examples of such methods are ion exchange using for example ion exchange resins or displacement of an acid counterion from its salt using another, usually stronger, acid. For example, treatment of a compound of formula (I), as defined hereinbefore, where $Z^-$ is $CF_3COO^-$, with HCl in a suitable solvent, such as water, methanol or diethyl ether, may produce a compound of formula 1, as defined hereinbefore, where $Z^-$ is $Cl^-$.

Certain compounds of formula (I), as defined hereinbefore, may contain groups that may be further converted into the salts thereof, for pharmaceutical use particularly into pharmaceutically acceptable salts with inorganic or organic acids and bases. Acids which may be used for this purpose include for example hydrochloric acid, hydrobromic acid, sulphuric acid, methanesulphonic acid, phosphoric acid, fumaric acid, succinic acid, lactic acid, citric acid, tartaric acid or maleic acid. Corresponding processes are known to the skilled person.

Moreover, where one or more stereoisomers may exist, the compounds of general formula (I) or intermediates in the synthesis of compounds of general formula (I) may be obtained as mixtures and then resolved into their stereoisomers, e.g. enantiomers and/or diastereomers. Thus, for example, cis/trans mixtures may be resolved into their cis and trans isomers, and racemic compounds may be separated into their enantiomers.

Thus, for example, the cis/trans mixtures may be resolved by chromatography into the cis and trans isomers thereof. The compounds of general formula (I) or intermediates in the synthesis of compounds of general formula 1, which occur as racemates may be separated by methods known per se (cf. Allinger N. L. and Eliel E. L. in "Topics in Stereochemistry", Vol. 6, Wiley Interscience, 1971) into their optical antipodes and compounds of general formula 1 or intermediates in the synthesis of compounds of general formula (I) with at least 2 asymmetric carbon atoms may be resolved into their diastereomers on the basis of their physical-chemical differences using methods known per se, e.g. by chromatography and/or fractional crystallisation, and, if these compounds are obtained in racemic form, they may subsequently be resolved into the enantiomers as mentioned above.

The racemates are preferably resolved by column chromatography on chiral phases or by crystallization from an optically active solvent or by reacting with an optically active substance which forms salts or derivatives such as esters or amides with the racemic compound. Salts may be formed with enantiomerically pure acids for basic compounds and with enantiomerically pure bases for acidic compounds. Diastereomeric derivatives are formed with enantiomerically pure auxiliary compounds, e.g. acids, their activated derivatives, or alcohols. Separation of the diastereomeric mixture of salts or derivatives thus obtained may be achieved by taking advantage of their different physico-chemical properties, e.g. differences in solubility; the free antipodes may be released from the pure diastereomeric salts or derivatives by the action of suitable agents. Optically active acids in common use for such a purpose are e.g. the D- and L-forms of tartaric acid, dibenzoyltartaric acid, ditoloyltartaric acid, malic acid, mandelic acid, camphorsulfonic acid, glutamic acid, aspartic acid, or quinic acid. Optically active alcohols applicable as auxiliary residues may be, for example, (+) or (−)-menthol and optically active acyl groups in amides may be, for example, (+)- or (−)-menthyloxycarbonyl.

The substances according to the invention are isolated and purified in a manner known per se, for example by distilling off the solvent under reduced pressure and recrystallizing the residue obtained from a suitable solvent or subjecting it to one of the customary purification methods, such as, for example, column chromatography on a suitable support material.

The compounds according to the invention are advantageously obtainable using the methods described in the examples that follow, which may also be combined for this purpose with methods known to the skilled person from his/her expert knowledge. Likewise, further compounds according to this invention, whose preparation are not explicitly described in the following examples, can be prepared analogously or similarly to the examples.

EXAMPLES

The following examples illustrate the present invention without restricting its scope.

Other features and advantages of the present invention will become apparent from the following more detailed Examples which illustrate, by way of example, the principles of the invention.

Where no salt forms of compounds are specified, the compound may exist as a free base or a salt or a zwitterion, depending on the chemical structure, the synthesis conditions and the processes of workup and purification applied. The skilled person will appreciate that the compound is not limited to a certain salt form. Where salt forms of compounds are specified, the stoichiometry of the counterion is usually omitted. In case of multiply charged counterions the skilled person will appreciate that the resulting salt form is uncharged, leading to the corresponding stoichiometry. The skilled person will appreciate that the compound is not limited to the mono salt form and that it may exist as a disalt, trisalt or other compound: counterion stoichiometries. Furthermore, the skilled person will appreciate that such compound may unexpectedly exist as a salt with a different counterion, depending on the synthesis conditions and the processes of workup and purification applied. Solely for the purpose of yield determination, an estimate of the nature of the counterion and of compound: counterion stoichiometry is made (as indicated by the formula given).

Synthesis of Intermediates

Intermediate A.1

3,5-diamino-6-chloropyrazine-2-carboxylic acid

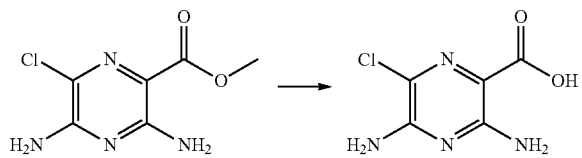

A.1

A mixture of methyl 3,5-diamino-6-chloropyrazine-2-carboxylate (100 g; 494 mmol), methanol (1 l) and NaOH (6 mol/l in water; 240 ml; 1.44 mol) is refluxed for 3 h. The mixture is allowed to cool to r.t. and then neutralized by addition of hydrochloric acid (6 mol/l in water; approx. 240 mL). Water (200 ml) is added. The precipitate formed is filtered off with suction, washed with water and dried at 60° C.

$C_5H_5ClN_4O_2$ ESI Mass spectrum: m/z=189 [M+H]+; m/z=187 [M−H]−

Intermediate A.2

3,5-Diamino-6-bromopyrazine-2-carboxylic acid

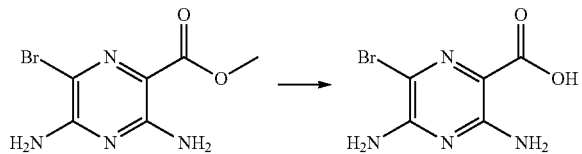

A.2

A.2 is prepared from methyl 3,5-diamino-6-bromopyrazine-2-carboxylate (which is prepared from methyl 3,5-diamino-6-chloropyrazine-2-carboxylate as described in J. Med. Chem. 10 (1967) 66-75) analogously to the procedure described for the synthesis of intermediate A.1

Intermediate B.1

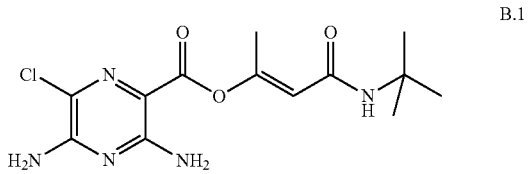 [SMILES: C/C(=C\C(=O)NC(C)(C)C)OC(=O)c1nc(Cl)c(N)nc1N]

B.1

Stage 1:
A mixture of tert-butanol (21.0 ml; 226 mmol) and 5-methylisoxazole (18.0 ml; 221 mmol) is cooled with an ice-bath. Trifluoromethanesulphonic acid (20.0 ml; 221 mmol) is added dropwise with continued cooling. The resulting mixture is stirred for 1 h without further cooling.
Stage 2:
To a solution or suspension of intermediate A.1 (14.0 g; 74.2 mmol) and triethylamine (31.0 ml; 222 mmol) in DMF (1400 ml) is added the mixture prepared in stage 1. The resulting mixture is stirred for 4 h at r.t. Ice-water is added with stirring. The precipitate formed is filtered off with suction, washed with water and dried at 65° C. to yield the title compound ($C_{13}H_{18}ClN_5O_3$).
TLC (Silica; DCM/MeOH 9:1): $R_f$=0.4
ESI Mass spectrum: m/z=328 [M+H]+; m/z=326 [M−H]−

Intermediate I.1

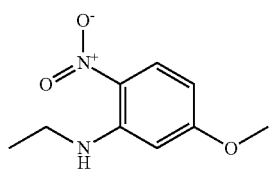

A mixture of 2-fluoro-4-methoxy-1-nitro-benzene (17.3 g; 0.10 mol) and ethylamine (2M in THF; 180 ml; 360 mmol) is stirred for 1 h at 90° C. (microwave heating). The mixture is diluted with water and extracted with ethyl acetate. The organic layer is separated, dried and evaporated.

I.1   $C_9H_{12}N_2O_3$ ESI Mass spectrum: m/z=197 [M+H]+

The following intermediates are prepared accordingly from the respective amines and the respective aryl halides as indicated. Depending upon conditions applied, the syntheses may yield a free base, a TFA salt or other salt forms which can be applied equally to further synthesis steps.

| Intermediate | Structure | Amine applied | Aryl halide applied | Synthesis comment |
|---|---|---|---|---|
| I.2 | 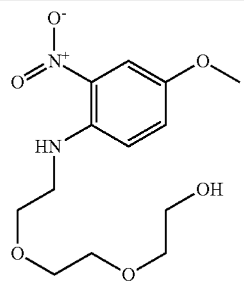 [SMILES: COc1ccc(NCCOCCOCCO)c([N+](=O)[O-])c1] | | | Reaction over night at 80° C.; 1.2 eq. of amine, K₂CO₃ applied as additional base |
| I.3 | 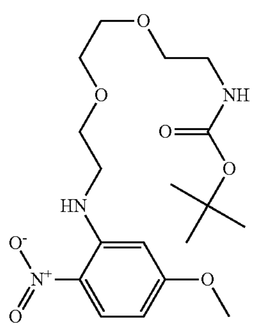 [SMILES: COc1ccc([N+](=O)[O-])c(NCCOCCOCCNC(=O)OC(C)(C)C)c1] | | | 2 eq. amine; solvent is methyl-THF; reaction over night at 60° C. |
| I.4 | 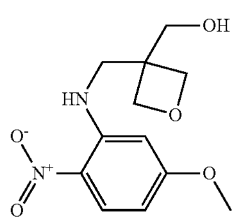 [SMILES: COc1ccc([N+](=O)[O-])c(NCC2(CO)COC2)c1] | | | 2 eq. amine; solvent is methyl-THF; reaction over night at 60° C. |
| I.5 | 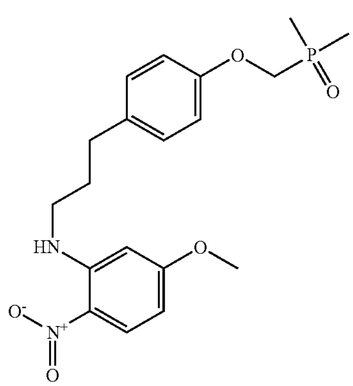 [SMILES: COc1ccc([N+](=O)[O-])c(NCCCc2ccc(OCP(C)(C)=O)cc2)c1] | II.12 | | Reaction over night at 60° C.; 1.2 eq. of amine, K₂CO₃ applied as additional base. Purification by silica gel chromatography (DCM/MeOH 0-> 5%) |

-continued

| Intermediate | Structure | Amine applied | Aryl halide applied | Synthesis comment |
|---|---|---|---|---|
| I.6 | 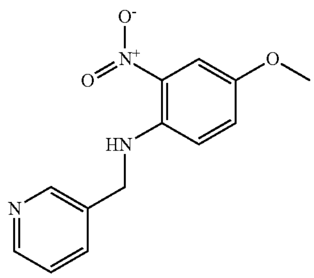 [SMILES: COc1ccc(NCc2cccnc2)c([N+](=O)[O-])c1] | | | Reaction for 1h at 100° C. (closed μ wave vessel); 3.1 eq. of amine. Purification by silica gel chromatography (DCM/MeOH 0- > 5%) |
| I.7 | 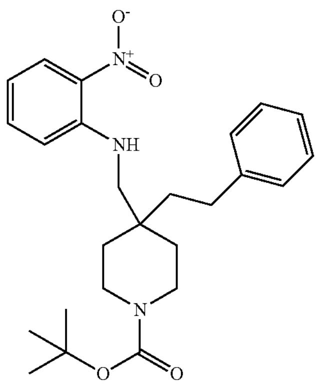 [SMILES: CC(C)(C)OC(=O)N1CCC(CCc2ccccc2)(CNc2ccccc2[N+](=O)[O-])CC1] | | | Reaction for 7h at 60° C.; 1 eq. of amine, K₂CO₃ applied as additional base |
| I.8 | 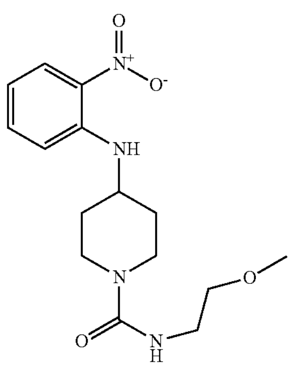 [SMILES: COCCNC(=O)N1CCC(Nc2ccccc2[N+](=O)[O-])CC1] | XVII.I | | Reaction for 7h at 60° C.; 1 eq. of amine, K₂CO₃ applied as additional base |
| I.9 | 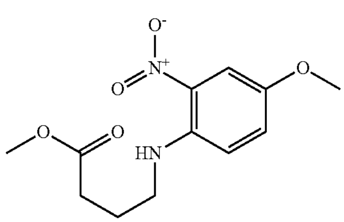 | | | Reaction over night at 80° C. in ACN; 1.2 eq. of amine, K₂CO₃ applied as additional base |
| I.10 | | | | Reaction at 70° C. overnight; 1 eq. of amine, K₂CO₃ applied as additional base. Crude product triturated with water, recrystallized from EE | a: Reaction in ACN at 160° C. (closed vessel, μ wave irradiation) for 3h with N,N-diisopropylethylamine added. Mixture is evaporated, taken up in acetic anhydride and stirred at 85° C. for 5h. Product purified by silica gel chromatography (DCM/CH 45- > 15%).

Intermediate II.1

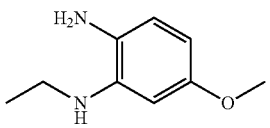

Intermediate I.1 (18.44 g; 0.09 mol) in THF (200 ml) is hydrogenated in a Parr apparatus (r.t., 50 psi hydrogen; catalyst: Pd/C 5%; 1.84 g). The catalyst is filtered off under nitrogen and the filtrate is applied directly to the next reaction step as described there.

The following intermediates are prepared accordingly from the respective starting materials as indicated. Depending upon conditions applied, the syntheses may yield a free base, a TFA salt or other salt forms which can be applied equally to further synthesis steps.

| Intermediate | Structure | Starting material applied | Synthesis comment |
|---|---|---|---|
| II.2 | 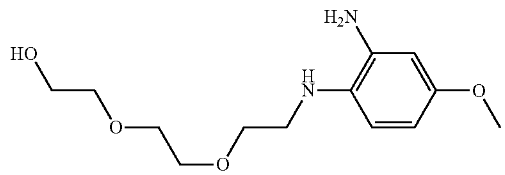 [SMILES: COc1ccc(NCCOCCOCCO)c(N)c1] | I.2 | Catalyst: Raney-Ni |
| II.3 | 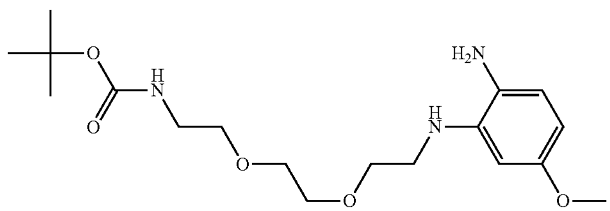 [SMILES: COc1ccc(N)c(NCCOCCOCCNC(=O)OC(C)(C)C)c1] | I.3 | Catalyst: Raney-Ni |
| II.4 | 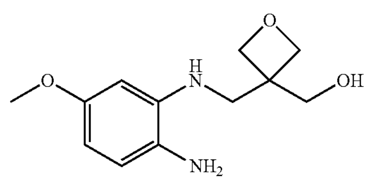 [SMILES: COc1ccc(N)c(NCC2(CO)COC2)c1] | I.4 | Catalyst: Raney-Ni |
| II.5 | 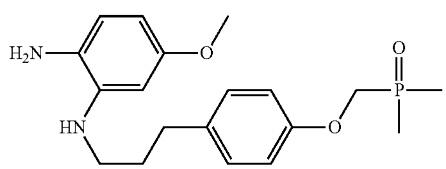 [SMILES: COc1ccc(N)c(NCCCc2ccc(OCP(C)(C)=O)cc2)c1] | I.5 | Catalyst: Raney-Ni |
| II.6 | 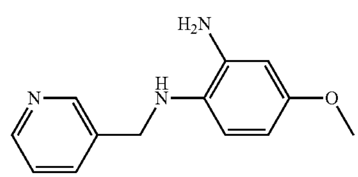 [SMILES: COc1ccc(NCc2cccnc2)c(N)c1] | I.6 | Catalyst: Raney-Ni |
| II.7 | 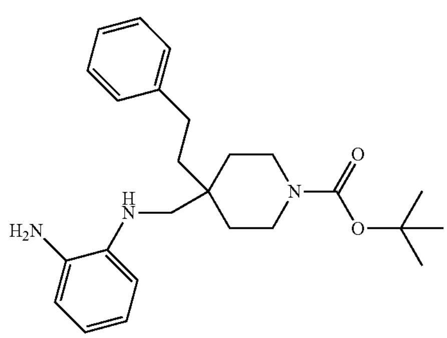 [SMILES: CC(C)(C)OC(=O)N1CCC(CCc2ccccc2)(CNc2ccccc2N)CC1] | I.7 | Solvent: EtOH |

-continued

| Intermediate | Structure | Starting material applied | Synthesis comment |
|---|---|---|---|
| II.8 | 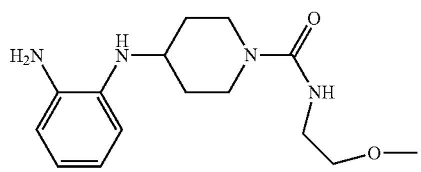 [SMILES: COCCNC(=O)N1CCC(Nc2ccccc2N)CC1] | I.8 | Solvent: EtOH |
| II.9 | 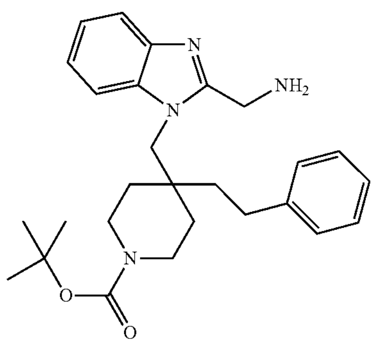 [SMILES: CC(C)(C)OC(=O)N1CCC(CCc2ccccc2)(Cn2c(CN)nc3ccccc32)CC1] | V.1 | Solvent: methanol |
| II.10 | 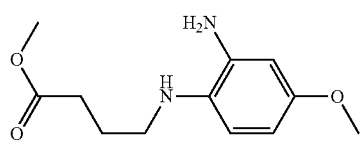 [SMILES: COC(=O)CCCNc1ccc(OC)cc1N] | I.9 | Catalyst: Raney-Ni; Solvent: methanol |
| II.11 | 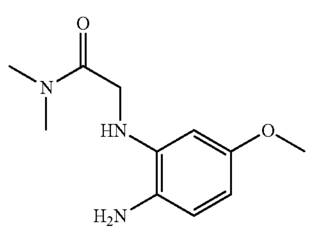 | I.10 | |
| II.12 | 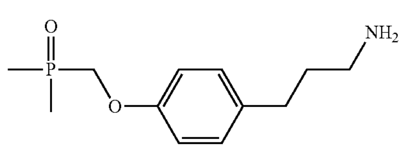 [SMILES: CP(C)(=O)COc1ccc(CCCN)cc1] | XV.1 | Catalyst: Raney-Ni; solvent: methanolic ammonia |

Intermediate III.1

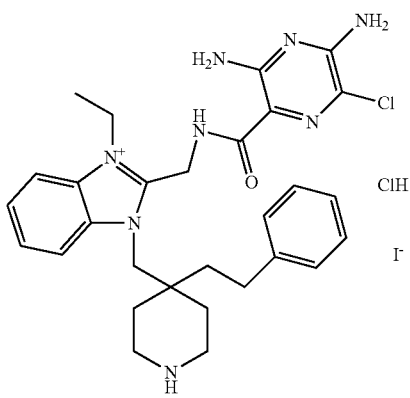

A mixture of intermediate VIII.5 (380 mg; 0.441 mmol), dioxane (10 ml) and aq. HCl (2 mol/l; 5.0 ml; 7.0 mmol) is stirred at r.t. for 2 h, then evaporated. The residue is taken up in diethyl ether and the precipitate is filtered and dried in vacuo.

$C_{29}H_{36}ClN_8O \times I \times HCl$ ESI Mass spectrum: m/z=547 [M]+

HPLC analytics: RT=3.50 min (HPLC method C)

Intermediate IV.1

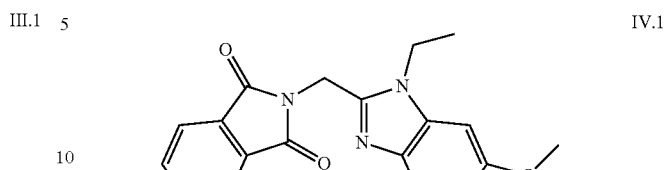

A mixture of the diaminobenzene intermediate II.1 (THF solution; theory: 15.6 g; 94.0 mmol), N-phthaloylglycine (19.3 g; 94.03 mmol), TBTU (33.2 g; 103 mmol) and TEA (14.3 ml; 103 mmol) is stirred at r.t. for 3 h. Water is added, the precipitate is filtered off, dried, and taken up in glacial acetic acid and refluxed for 2 h. The mixture is evaporated. The residue is taken up in water and extracted with ethyl acetate. The organic layer is separated, dried and evaporated. The residue (if solid) is refluxed in ethyl acetate, cooled to r.t., filtered off, washed with ethyl acetate and dried.

$C_{19}H_{17}N_3O_3$ ESI Mass spectrum: m/z=336 [M+H]+

The following intermediates are prepared accordingly from the respective diaminobenzenes as indicated. Depending upon conditions applied, the syntheses may yield a free base, a TFA salt or other salt forms which can be applied equally to further synthesis steps.

| Intermediate | Structure | Diamino-benzene applied | Synthesis comment |
|---|---|---|---|
| IV.2 | 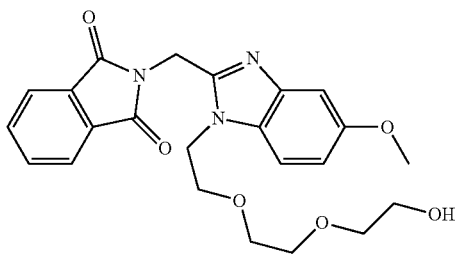 [SMILES: COc1ccc2c(c1)nc(CN1C(=O)c3ccccc3C1=O)n2CCOCCOCCO] | II.2 | Footnote a) |
| IV.3 | 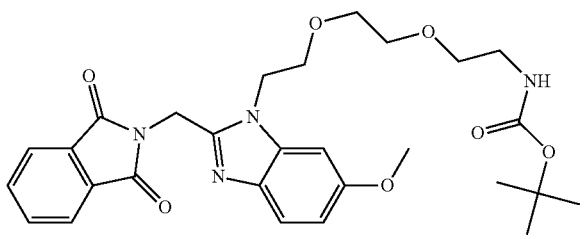 [SMILES: COc1ccc2nc(CN3C(=O)c4ccccc4C3=O)n(CCOCCOCCNC(=O)OC(C)(C)C)c2c1] | II.3 | Ring closing step: reaction in dioxane/HOAc 3:1 for 3 d at 85° C. |
| IV.4 | 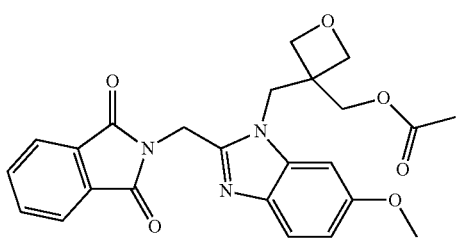 [SMILES: COc1ccc2nc(CN3C(=O)c4ccccc4C3=O)n(CC3(COC(C)=O)COC3)c2c1] | II.4 | Ring closing step: refluxed in HOAc overnight. Product purified by silica gel chromatography (DCM/MeOH 0->8%). |

| Intermediate Structure | Diaminobenzene applied | Synthesis comment |
|---|---|---|
| IV.5 | II.5 | |
| IV.6 | II.6 | Product purified by silica gel chromatography (DCM/MeOH 0->8%). |
| IV.7 | II.11 | Footnote a | a) No precipitate, therefore taken up in water and extracted with ethyl acetate. Organic layer evaporated, residue stirred in dioxane/4M HCl at 95° C. over night. Upon evaporation, taken up in K₂CO₃ solution and extracted with ethyl acetate. Organic layer dried (MgSO₄) and evaporated.

Intermediate V.1

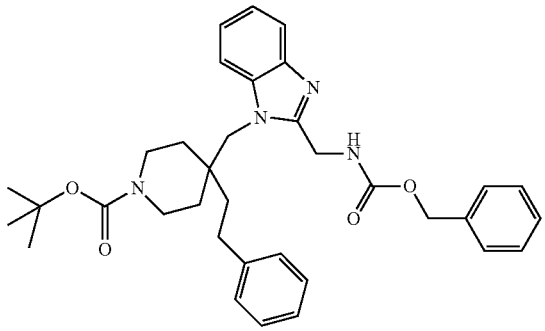

V.1

Step 1: To a solution of the diaminobenzene intermediate II.7 (6.60 g; 15.8 mmol) in THF (70 ml) is added N-Cbz-Glycine (3.30 g; 15.8 mmol), TBTU (5.07 g; 15.8 mmol) and triethylamine (2.42 ml; 17.4 mmol). The mixture is stirred at RT overnight, then water is added and the mixture is extracted with ethyl acetate. The organic layer is separated, dried (MgSO₄) and evaporated.

Step 2: The residue is taken up in acetic acid (70 ml) and stirred overnight at 80° C. The mixture is evaporated, taken up in ethyl acetate, extracted with sodium bicarbonate solution, then with water. The organic layer is dried (MgSO₄), filtered and evaporated to yield the product.

$C_{35}H_{42}N_4O_4$ ESI Mass spectrum: m/z=583 [M+H]+

The following intermediates are prepared accordingly from the respective diaminobenzene and glycine derivative as indicated. Depending upon conditions applied, the syntheses may yield a TFA salt or other salt forms which can be applied equally to further synthesis steps.

| Intermediate | Structure | Diaminobenzene applied | Glycine derivative applied | Synthesis comment |
|---|---|---|---|---|
| V.2 | H₂N-CH₂-benzimidazole-N-(CH₂)₃-C(O)-OCH₃, OMe substituent; HCl salt | II.10 | HOOC-CH₂-NH-Boc | Step 2: reaction in dioxane at 70° C. for 30 min with 1.5 eq. toluenesulfonic acid added; then stirred overnight in DCM/HCl (4 mol/l in dioxane). Product precipitates. |

Intermediate VI.1

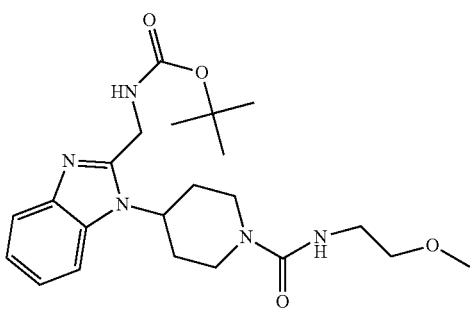

To a mixture of the diaminobenzene intermediate II.8 (540 mg; 1.81 mmol), DMF (10 ml) and water (1.5 ml) is added dropwise a mixture of N—BOC-2-aminoethanal (607 mg, 3.62 mmol) and DMF (15 ml). Acetic acid (261 µl, 4.34 mmol) is added and the mixture is stirred at RT overnight under air atmosphere. Solvents are evaporated, the residue is taken up in DCM and extracted with water. The organic layer is separated, dried (Na₂SO₄) and evaporated. The crude product is purified by silica gel chromatography (DCM/MeOH 0→8%)

$C_{22}H_{33}N_5O_4$ ESI Mass spectrum: m/z=432 [M+H]+

Intermediate VII.1

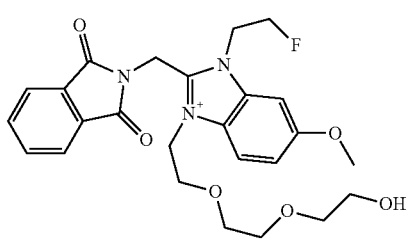 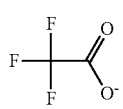

A mixture of intermediate IV.2 (1.30 g; 2.96 mmol), 1-bromo-2-fluoroethane (0.854 ml; 11.8 mmol), potassium carbonate (0.818 g; 5.92 mmol), potassium iodide (0.982 g; 5.92 mmol) and acetonitrile (20 ml) is stirred at 140° C. (closed vessel, wave irradiation) for 10 h. Insolubles are filtered off by suction, is the filtrate is evaporated and purified by RP-HPLC (Sunfire, water/ACN/TFA).

$C_{25}H_{29}FN_3O_6 \times C_2O_2F_3$ ESI Mass spectrum: m/z=486 [M]+

HPLC analytics: RT=0.41 min (HPLC method A)

Intermediate VIII.1

A mixture of intermediate IV.3 (2.00 g; 3.71 mmol), the alkylating agent iodoethane (1.50 ml; 18.6 mmol) and ACN (15 ml) is stirred at 120° C. (closed vessel, wave irradiation) for 2 h. The mixture is evaporated to dryness.

$C_{30}H_{39}N_4O_7 \times I$ ESI Mass spectrum: m/z=567 [M]+

The following intermediates are prepared accordingly from the respective benzimidazoles as indicated. Depending upon conditions applied, the syntheses may yield a TFA salt or other salt forms which can be applied equally to further synthesis steps.

| Intermediate | Structure | Benzimidazole applied | Synthesis comment |
|---|---|---|---|
| VIII.2 | 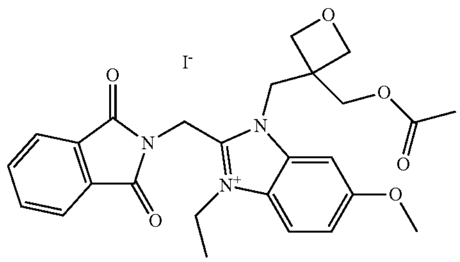 [SMILES: CC[n+]1c(CN2C(=O)c3ccccc3C2=O)n(CC2(COC(C)=O)COC2)c2cc(OC)ccc21 ; [I-]] | IV.4 | |
| VIII.3 | 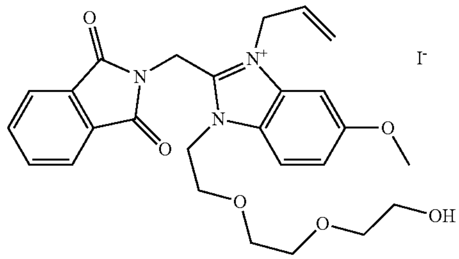 [SMILES: C=CC[n+]1c(CN2C(=O)c3ccccc3C2=O)n(CCOCCOCCO)c2ccc(OC)cc21 ; [I-]] | IV.2 | Allyl iodide applied as alkylating agent |
| VIII.4 | 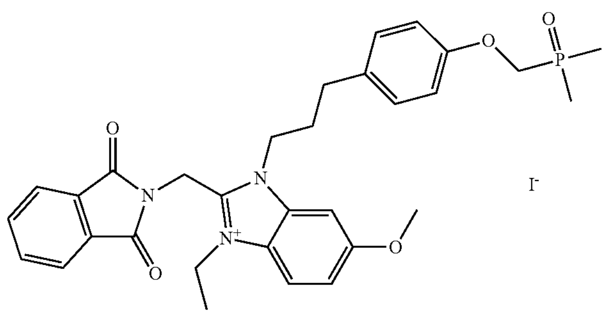 [SMILES: CC[n+]1c(CN2C(=O)c3ccccc3C2=O)n(CCCc2ccc(OCP(C)(C)=O)cc2)c2cc(OC)ccc21 ; [I-]] | IV.5 | |
| VIII.5 | 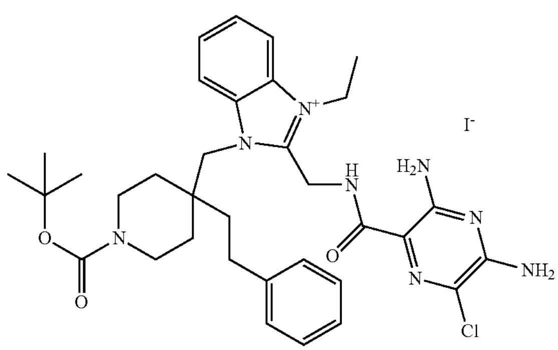 [SMILES: CC[n+]1c(CNC(=O)c2nc(Cl)c(N)nc2N)n(CC2(CCc3ccccc3)CCN(C(=O)OC(C)(C)C)CC2)c2ccccc21 ; [I-]] | XII.1 | Reaction at 100° C. for 8 h. Product triturated with diethyl ether |
| VIII.6 | 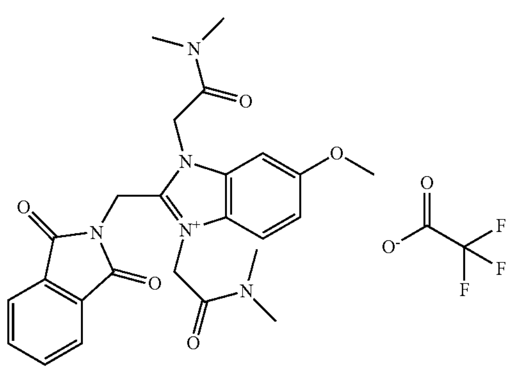 [SMILES: COc1ccc2c(c1)n(CC(=O)N(C)C)c(CN1C(=O)c3ccccc3C1=O)[n+]2CC(=O)N(C)C ; O=C([O-])C(F)(F)F] | IV.7 | N,N-dimethylbromoacetamide applied as alkylating agent; purification by RP-HPLC (modifier: TFA) |

Intermediate IX.1

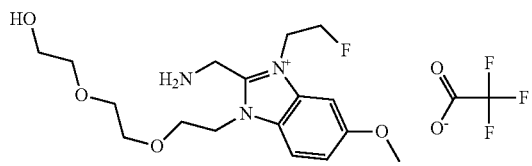

IX.1

A mixture of intermediate VII.1 (0.430 g; 0.574 mmol), hydrazine hydrate (0.112 ml; 2.30 mmol) and ACN (10 ml) is stirred overnight at 65° C. (bath temperature). Insolubles are filtered off by suction, the filtrate is evaporated and purified by RP-HPLC (Sunfire, water/ACN/TFA).

$C_{17}H_{27}FN_3O_4 \times C_2O_2F_3$

HPLC analytics: RT=0.27 min (HPLC method A)

The following intermediates are prepared accordingly from the respective protected amines as indicated. Depending upon conditions applied, the syntheses may yield a TFA salt or other salt forms which can be applied equally to further synthesis steps.

| Intermediate | Structure | Protected amine applied | Synthesis comment |
|---|---|---|---|
| IX.2 | 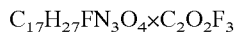 | VIII.1 | |
| IX.3 | 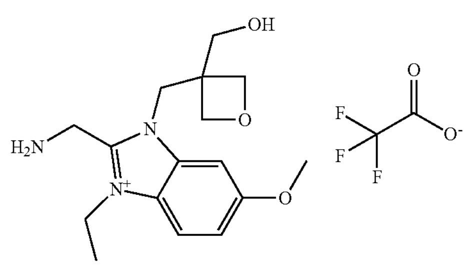 [SMILES: CC[n+]1c(CN)n(CC2(CO)COC2)c2cc(OC)ccc21 ; O=C([O-])C(F)(F)F] | VIII.2 | 10 eq. hydrazine hydrate applied |
| IX.4 | 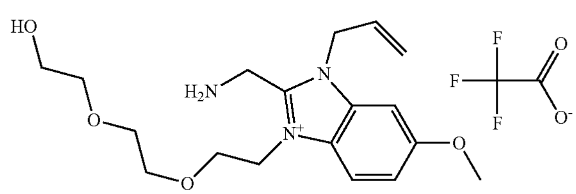 [SMILES: C=CCn1c(CN)[n+](CCOCCOCCO)c2ccc(OC)cc21 ; O=C([O-])C(F)(F)F] | VIII.3 | |
| IX.5 | 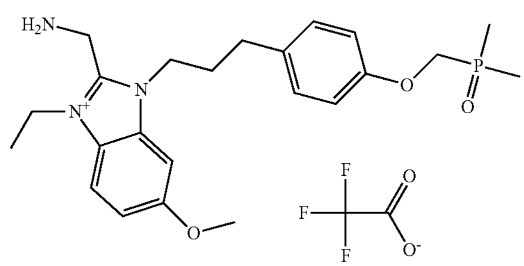 [SMILES: CC[n+]1c(CN)n(CCCc2ccc(OCP(C)(C)=O)cc2)c2cc(OC)ccc21 ; O=C([O-])C(F)(F)F] | VIII.4 | |

| Intermediate | Structure | Protected amine applied | Synthesis comment |
|---|---|---|---|
| IX.6 | 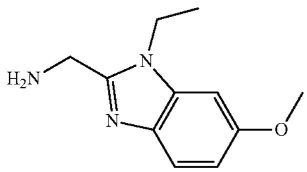 | IV.1 | Solvent: ethanol |
| IX.7 | 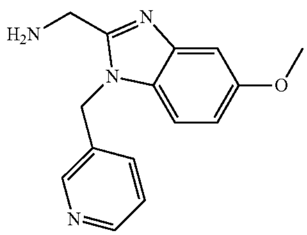 [SMILES: COc1ccc2c(c1)nc(CN)n2Cc1cccnc1] | IV.6 | Solvent: ethanol |
| IX.8 | 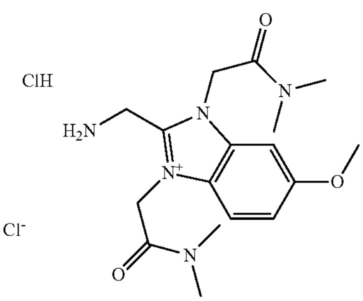 [SMILES: [Cl-] ; Cl ; COc1ccc2c(c1)n(CC(=O)N(C)C)c(CN)[n+]2CC(=O)N(C)C] | VIII.6 | Reaction at RT for 5 days. Product taken up in methanolic HCl and evaporated to dryness. |

Intermediate X.1

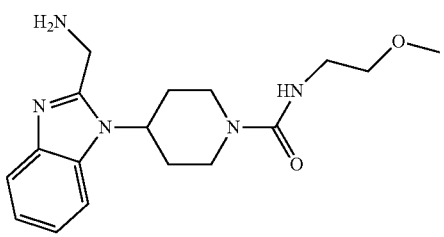

X.1

To a suspension of intermediate VI.1 (630 mg; 1.39 mmol) in DCM (10 ml) is added hydrochloric acid (4 mol/l in dioxane, 3.47 ml; 13.9 mmol). The mixture is stirred at RT for 2 h, then evaporated to dryness. The residue is dissolved in methanol and purified by ion exchange chromatography (strong cation exchange column (20 g), elution with ammonia (7 mol/l in methanol)).

$C_{17}H_{25}N_5O_2$ ESI Mass spectrum: m/z=332 [M+H]+

HPLC analytics: RT=0.59 min (HPLC method F)

Intermediate XI.1

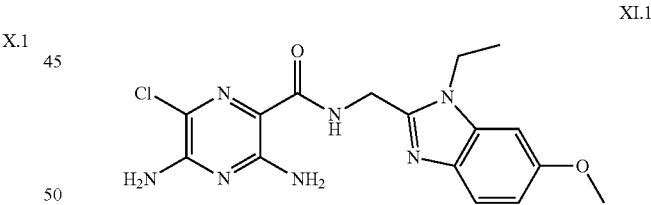

XI.1

A mixture of the acid intermediate A. 1 (5.60 g; 29.7 mmol), the primary amine intermediate IX.6 (6.10 g; 29.7 mmol), HATU (11.3 g; 29.7 mmol), triethylamine (8.24 ml; 59.4 mmol) and DMF (50 ml) is stirred overnight at RF. The mixture is poured on $Na_2CO_3$ solution, the precipitate is filtered off with suction and dried (50° C.).

$C_{16}H_{18}ClN_7O_2$ ESI Mass spectrum: m/z=376 [M+H]+

HPLC analytics: RT=0.72 min (HPLC method B)

The following intermediates are prepared accordingly from the respective amines as indicated. Depending upon conditions applied, the syntheses may yield a TFA salt or other salt forms which can be applied equally to further synthesis steps.

| Intermediate | Structure | Acid applied | amine applied | Synthesis comment |
|---|---|---|---|---|
| XI.2 | 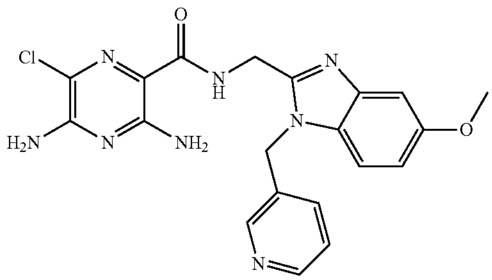 [SMILES: COc1ccc2c(c1)nc(CNC(=O)c1nc(Cl)c(N)nc1N)n2Cc1cccnc1] | A.1 | IX.7 | purified by RP-HPLC (modifier: TFA) |
| XI.3 | 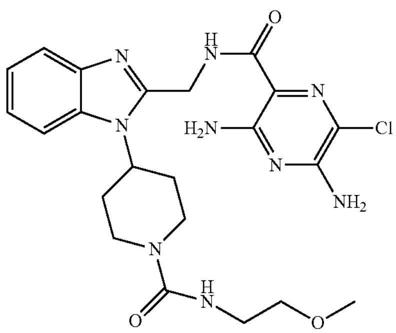 [SMILES: COCCNC(=O)N1CCC(n2c(CNC(=O)c3nc(Cl)c(N)nc3N)nc3ccccc32)CC1] | A.1 | X.1 | purified by RP-HPLC (modifier: TFA) |
| XI.4 | 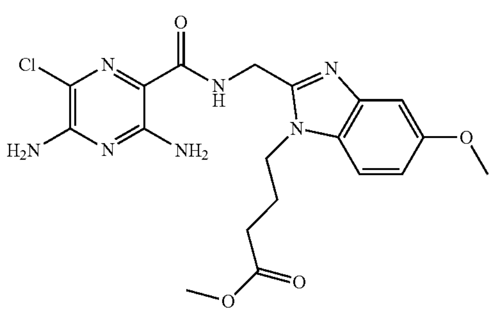 [SMILES: COC(=O)CCCn1c(CNC(=O)c2nc(Cl)c(N)nc2N)nc2cc(OC)ccc21] | A.1 | V.2 | Purified by silica gel chromatography (DCM/MeOH 1.5%) |
| XI.5 | 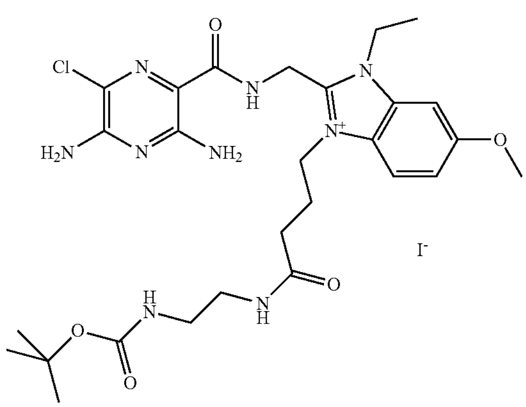 [SMILES: CCn1c(CNC(=O)c2nc(Cl)c(N)nc2N)[n+](CCCC(=O)NCCNC(=O)OC(C)(C)C)c2ccc(OC)cc21 ; [I-]] | XIV.2 | | purified by RP-HPLC (modifier: TFA) |

Intermediate XII.1

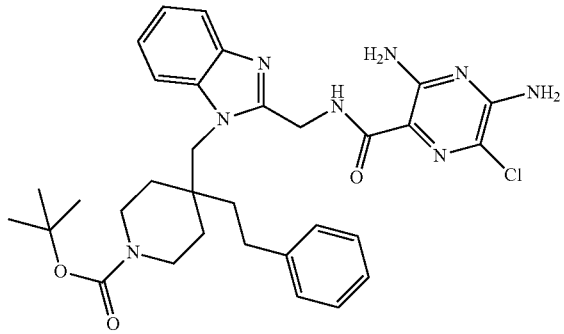

XII.1

To a solution of Intermediate II.9 (750 mg; 1.61 mmol) in DMF (10 ml) is added Intermediate B.1 (631 mg; 1.93 mmol). The mixture is stirred overnight at RT, then evaporated. The residue is taken up in DCM and extracted with water. The organic layer is separated, dried ($Na_2SO_4$), filtered and evaporated. The crude product is purified by silica gel chromatography (DCM/MeOH 0→4%).

$C_{32}H_{39}ClN_8O_3$ ESI Mass spectrum: m/z=619 [M+H]+
HPLC analytics: RT=4.61 min (HPLC method C)

Intermediate XIII.1

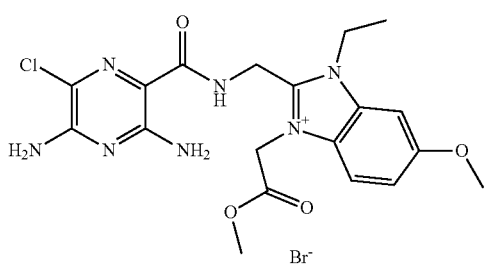

XIII.1

To a mixture of intermediate XI.1 (2.00 g; 5.32 mmol), triethylamine (742 µl (5.32 mmol) and ACN (15 ml) is added di-tert-Butyldicarbonate (1.74 g, 7.98 mmol). The mixture is stirred for 2 min, then bromoacetic acid methyl ester (14.8 ml, 160 mmol) is added and the mixture is stirred for 3 h at 80° C. After cooling down to RT, the precipitate is filtered off with suction and successively washed with ACN and diethyl ether.

$C_{19}H_{23}ClN_7O_4 \times Br$ ESI Mass spectrum: m/z=448 [M]+
HPLC analytics: RT=0.75 min (HPLC method B)

The following intermediates are prepared accordingly from the respective benzimidazole as indicated. Depending upon conditions applied, the syntheses may yield a TFA salt or other salt forms which can be applied equally to further synthesis steps.

| Intermediate | Structure | benzimidazole applied | Synthesis comment |
|---|---|---|---|
| XIII.2 | 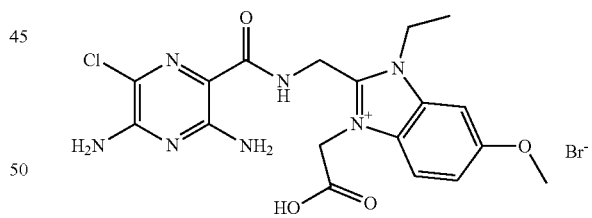 | XI.4 | purified by RP-HPLC (modifier: TFA) |

Intermediate XIV.1

XIV.1

A mixture of the ester intermediate XIII.1 (1.00 g; 1.89 mmol), NaOH (1.42 ml; 4.0 mol/l; 5.67 mmol), water (20 ml) and methanol (35 ml) is stirred for 3 h at 60° C., then overnight at RT. The mixture is neutralized by addition of aqueous hydrochloric acid (1 mol/1), then partly evaporated. The precipitate is filtered off with suction and successively washed with ethanol and diethyl ether.

$C_{18}H_{21}ClN_7O_4 \times Br$ ESI Mass spectrum: m/z=434 [M]+
HPLC analytics: RT=0.73 min (HPLC method B)

The following intermediates are prepared accordingly from the respective ester as indicated. Depending upon conditions applied, the syntheses may yield a TFA salt or other salt forms which can be applied equally to further synthesis steps.

| Intermediate | Structure | Ester applied | Synthesis comment |
|---|---|---|---|
| XIV.2 | 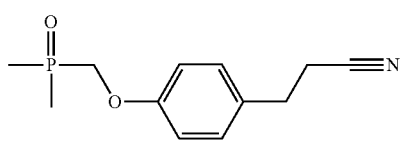 | XIII.2 | |

Intermediate XV.1

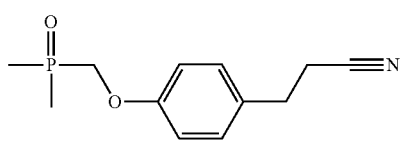

A mixture of 3-(4-hydroxyphenyl)propionitrile (6.20 g; 42.1 mmol), chloromethyl(dimethyl)-phosphine oxide (10.7 g; 84.2 mmol), potassium carbonate (17.5 g; 1256 mmol), NaI (6.31 g; 42.1 mmol) and acetone (100 ml) is stirred at 80° C. overnight, then evaporated. The residue is taken up in EE and extracted with water. The organic layer is separated, dried ($Na_2SO_4$) and evaporated.

TLC: $R_f$=0.5 (silica; DCM/methanol 9:1)

Intermediate XVI.1

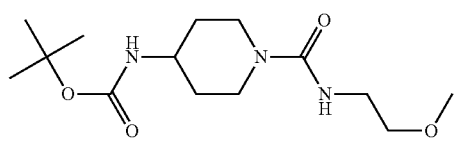

A mixture of tert-butyl-N-(4-piperidinyl)carbamate (4.00 g; 20.0 mmol), CDI (4.86 g; 30.0 mmol) and THF (15 ml) is stirred at 0° C. for 30 min. Triethylamine (5.55 ml; 39.9 mmol) and 2-methoxyethylamine (3.49 ml; 39.9 mmol) are added and the mixture is heated to 70° C. for 2 days. The mixture is evaporated, the residue is taken up in DCM, extracted successively with aq. $NaHCO_3$ and brine. The organic layer is evaporated to dryness.

$C_{14}H_{24}N_3O_4$ ESI Mass spectrum: m/z=302 [M+H]+

Intermediate XVII.1

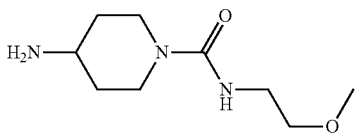

A mixture of intermediate XVI.1 (2.00 g; 5.31 mmol), TFA (7.4 ml) and DCM (40 ml) is stirred at r.t. for 6 h. The mixture is evaporated to dryness and the residue is subject to ion exchange chromatography (strong cation exchange cartridge (20 g); elution with ammonia (3.5 mol/l in methanol)).

Synthesis of Examples

Example 1.01

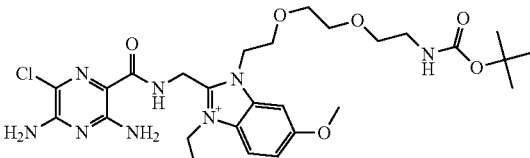

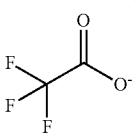

The amine intermediate IX.2 (300 mg; 0.436 mmol) is added to a mixture of intermediate A.1 (83.0 mg; 0.440 mmol), TBTU (141 mg; 0.440 mmol), triethylamine (185.0 µl; 1.32 mmol) and DMF (3.0 ml). The mixture is stirred at r.t. overnight, then evaporated and the crude product is purified by RP-HPLC (modifier: TFA).

$C_{27}H_{40}ClN_8O_6 \times C_2F_3O_2$ ESI Mass spectrum: m/z=607 [M]+

HPLC analytics: RT=0.82 min (HPLC method B)

The following example compounds are prepared accordingly from intermediate A.1 and the respective amine intermediate as indicated. Depending upon conditions applied, the syntheses may yield a TFA salt, a zwitterion or other salt forms.

| Example No. | Structure | Amine applied | M+ | RT (min) | HPLC Method |
|---|---|---|---|---|---|
| 1.02 | 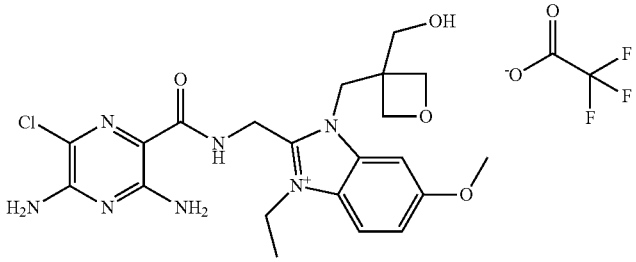 | IX.3 | 476 | 0.43 | D |
| 1.03 | 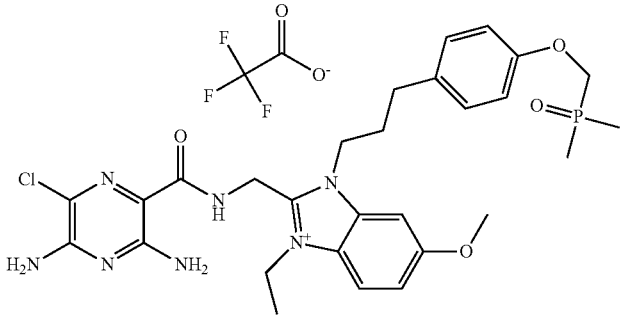 [SMILES: CC[n+]1c(CNC(=O)c2nc(Cl)c(N)nc2N)n(CCCc2ccc(OCP(C)(C)=O)cc2)c2cc(OC)ccc21 ; O=C([O-])C(F)(F)F] | IX.5 | 600 | 0.58 | E |
| 1.04 | 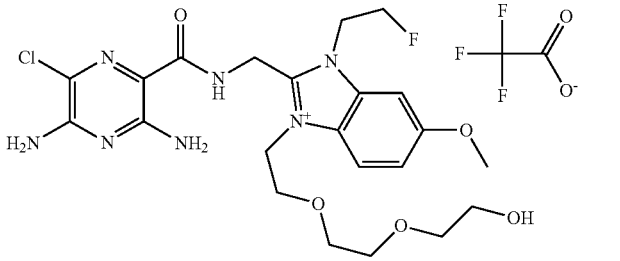 [SMILES: COc1ccc2c(c1)n(CCF)c(CNC(=O)c1nc(Cl)c(N)nc1N)[n+]2CCOCCOCCO ; O=C([O-])C(F)(F)F] | IX.1 | 526 | 0.39 | A |
| 1.05 | 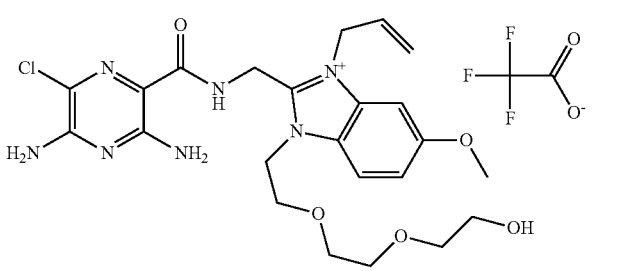 [SMILES: C=CC[n+]1c(CNC(=O)c2nc(Cl)c(N)nc2N)n(CCOCCOCCO)c2ccc(OC)cc21 ; O=C([O-])C(F)(F)F] | IX.4 | 520 | 0.41 | A |
| 1.06 | 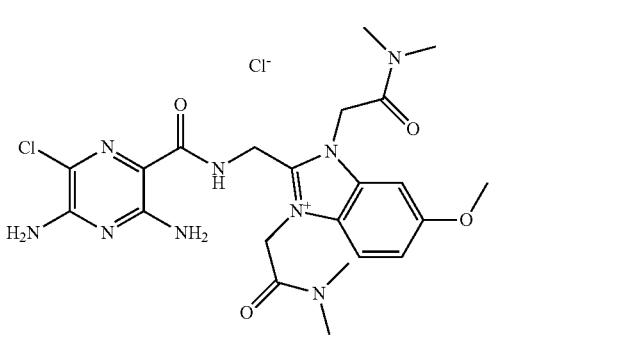 [SMILES: COc1ccc2c(c1)n(CC(=O)N(C)C)c(CNC(=O)c1nc(Cl)c(N)nc1N)[n+]2CC(=O)N(C)C ; [Cl-]] | IX.8 | 518 | 0.36 | A |

Example 2.01

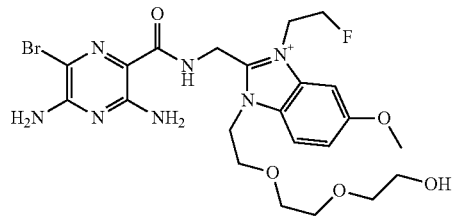

2.01

The compound is prepared from intermediate IX.1 and intermediate A.2 according to the procedure described for example 1.01.

$C_{22}H_{30}BrFN_7O_5 \times C_2F_3O_2$ ESI Mass spectrum: m/z=570 [M]+

HPLC analytics: RT=0.74 min (HPLC method B)

Example 3.01

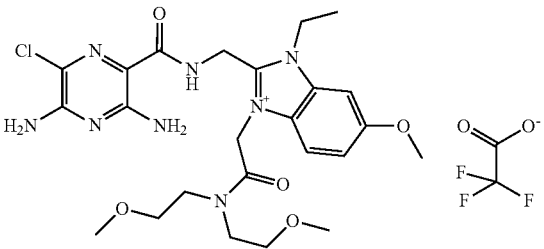

3.01

The amine di(methoxyethyl)amine (20.7 mg; 0.155 mmol) is added to a mixture of the acid intermediate XIV.1 (40.0 mg; 0.078 mmol), HATU (59.1 mg; 0.155 mmol), triethylamine (21.5 µl; 0.155 mmol) and DMF (2.0 ml). The mixture is stirred at 60° C. for 1 h, then evaporated. The crude product is purified by RP-HPLC (modifier: TFA).

$C_{24}H_{34}ClN_8O_5 \times C_2F_3O_2$ ESI Mass spectrum: m/z=549 [M]+

HPLC analytics: RT=0.79 min (HPLC method B)

The following example compounds are prepared accordingly from the respective amine and intermediate XIV.1 as indicated. Depending upon conditions applied, the syntheses may yield a TFA salt, a zwitterion or other salt forms.

| Example No. | Structure | Amine applied | M+ | RT (min) | HPLC Method |
|---|---|---|---|---|---|
| 3.02 | 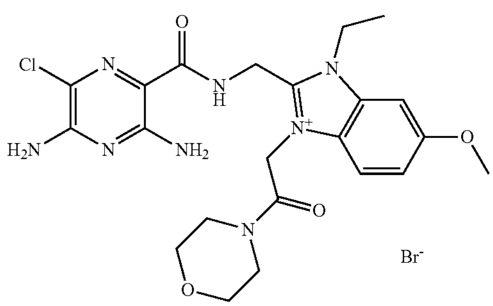 [SMILES: CCn1c(CNC(=O)c2nc(Cl)c(N)nc2N)[n+](CC(=O)N2CCOCC2)c2ccc(OC)cc21 ; [Br-]] | morpholine | 503 | 0.73 | B |
| 3.03 | 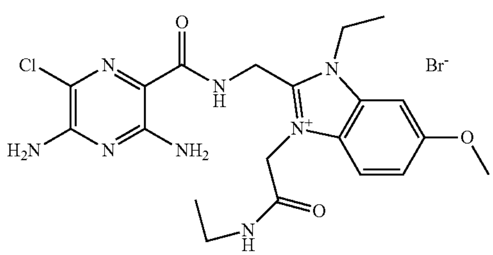 [SMILES: CCNC(=O)C[n+]1c(CNC(=O)c2nc(Cl)c(N)nc2N)n(CC)c2cc(OC)ccc21 ; [Br-]] | ethylamine (2 mol/l in THF) | 461 | 0.74 | B |
| 3.04 | 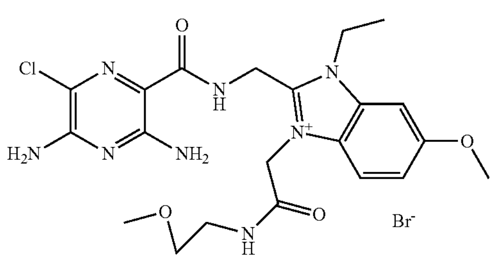 [SMILES: CCn1c(CNC(=O)c2nc(Cl)c(N)nc2N)[n+](CC(=O)NCCOC)c2ccc(OC)cc21 ; [Br-]] | 2-methoxyethyl-amine | 491 | 0.73 | B |

-continued
| Example No. | Structure | Amine applied | M+ | RT (min) | HPLC Method |
|---|---|---|---|---|---|
| 3.05 | 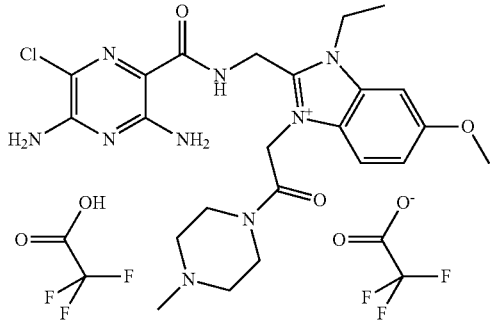 [SMILES: O=C(O)C(F)(F)F ; CCn1c(CNC(=O)c2nc(Cl)c(N)nc2N)[n+](CC(=O)N2CCN(C)CC2)c2ccc(OC)cc21 ; O=C([O-])C(F)(F)F] | 1-methyl-piperazine | 516 | 0.65 | B |
| 3.06 | 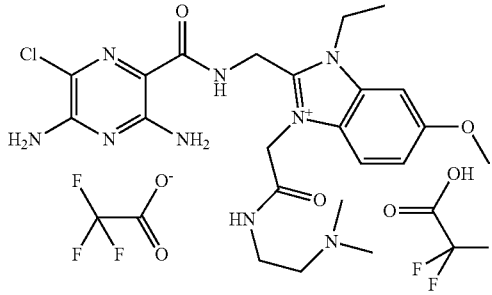 | 2-dimethyl-amino-ethylamine | 504 | 0.66 | B |
| 3.07 | 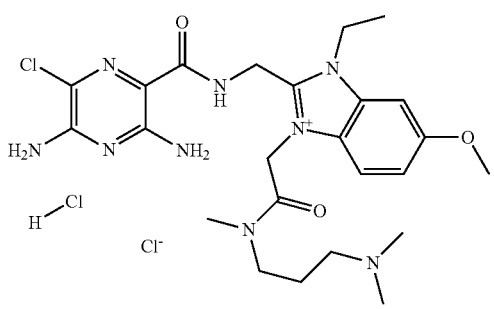 [SMILES: CCn1c(CNC(=O)c2nc(Cl)c(N)nc2N)[n+](CC(=O)N(C)CCCN(C)C)c2ccc(OC)cc21 ; Cl ; [Cl-]] | N-methyl-3-(dimethyl-amino)-propylamine | 532 | 0.66 | B |
| 3.08 | 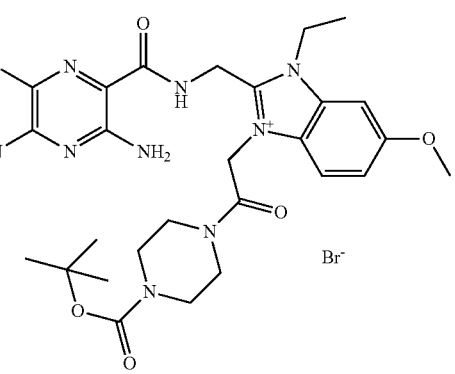 | 1-tert-butoxy-carbonyl-piperazine | 602 | 0.84 | B |

| Example No. | Structure | Amine applied | M+ | RT (min) | HPLC Method |
|---|---|---|---|---|---|
| 3.09 | 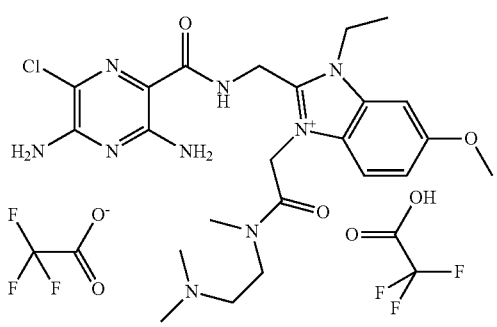 [SMILES: O=C([O-])C(F)(F)F ; CCn1c(CNC(=O)c2nc(Cl)c(N)nc2N)[n+](CC(=O)N(C)CCN(C)C)c2ccc(OC)cc21 ; O=C(O)C(F)(F)F] | N-methyl-3-(dimethyl-amino)-ethylamine | 518 | 0.65 | B |
| 3.10 | 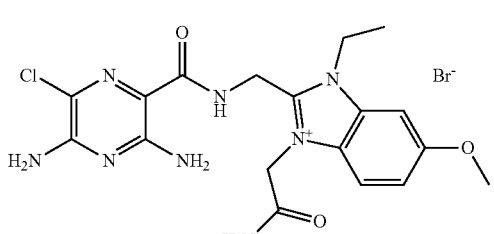 | aq. ammonia (32%) | 433 | 0.71 | B |
| 3.11 | 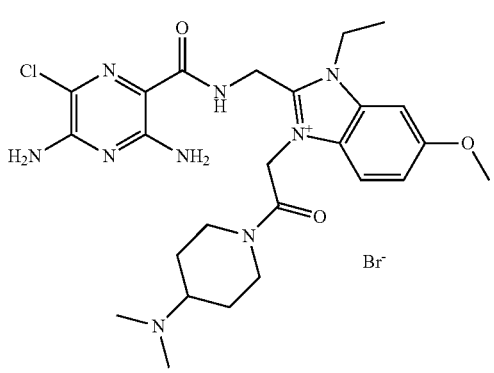 [SMILES: CCn1c(CNC(=O)c2nc(Cl)c(N)nc2N)[n+](CC(=O)N2CCC(N(C)C)CC2)c2ccc(OC)cc21 ; [Br-]] | 4-(dimethyl-amino)-piperidine | 544 | 0.64 | B |
| 3.12 | 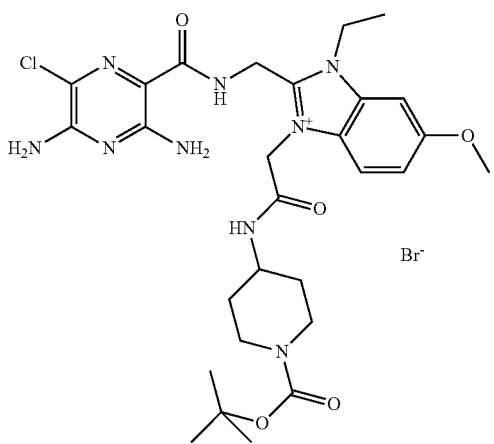 [SMILES: CCn1c(CNC(=O)c2nc(Cl)c(N)nc2N)[n+](CC(=O)NC2CCN(C(=O)OC(C)(C)C)CC2)c2ccc(OC)cc21 ; [Br-]] | 1-tert-butoxy-carbonyl-4-amino-piperidine | 616 | 0.88 | B |

| Example No. | Structure | Amine applied | M+ | RT (min) | HPLC Method |
|---|---|---|---|---|---|
| 3.13 | 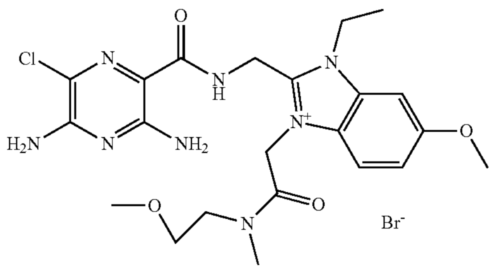 [SMILES: CCn1c(CNC(=O)c2nc(Cl)c(N)nc2N)[n+](CC(=O)N(C)CCOC)c2ccc(OC)cc21 ; [Br-]] | N-methyl-2-methoxy-ethylamine | 505 | 0.76 | B |
| 3.14 | 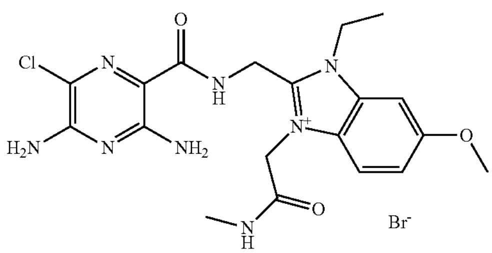 [SMILES: CCn1c(CNC(=O)c2nc(Cl)c(N)nc2N)[n+](CC(=O)NC)c2ccc(OC)cc21 ; [Br-]] | methylamine (2 mol/l in THF) | 447 | 0.71 | B |
| 3.15 | 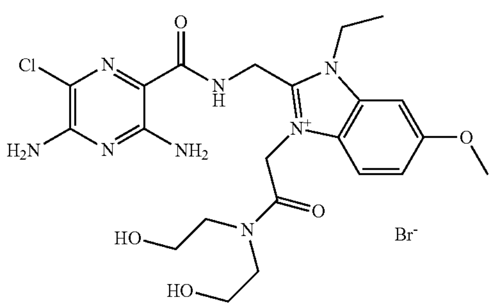 [SMILES: CCn1c(CNC(=O)c2nc(Cl)c(N)nc2N)[n+](CC(=O)N(CCO)CCO)c2ccc(OC)cc21 ; [Br-]] | Diethanol-amine | 521 | 0.71 | B |
| 3.16 | 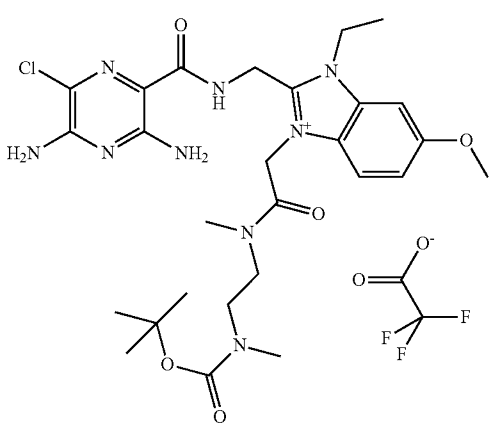 [SMILES: CCn1c(CNC(=O)c2nc(Cl)c(N)nc2N)[n+](CC(=O)N(C)CCN(C)C(=O)OC(C)(C)C)c2ccc(OC)cc21 ; O=C([O-])C(F)(F)F] | methyl-(2-methylamino-ethyl)-carbamic acid tert-butyl ester | 604 | 0.85 | B |

-continued

| Example No. | Structure | Amine applied | M+ | RT (min) | HPLC Method |
|---|---|---|---|---|---|
| 3.17 | 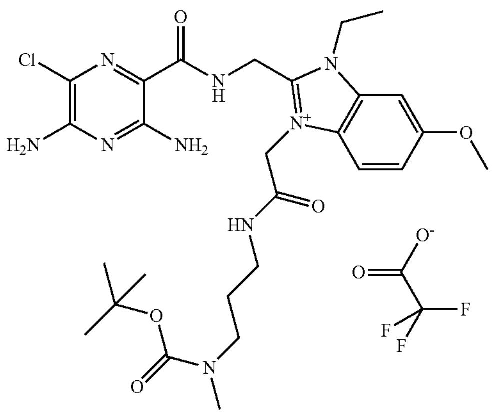 [SMILES: CCn1c(CNC(=O)c2nc(Cl)c(N)nc2N)[n+](CC(=O)NCCCN(C)C(=O)OC(C)(C)C)c2ccc(OC)cc21 ; O=C([O-])C(F)(F)F] | methyl-(3-amino-propyl)-carbamic acid tert-butyl ester | 604 | 0.86 | B |
| 3.18 | 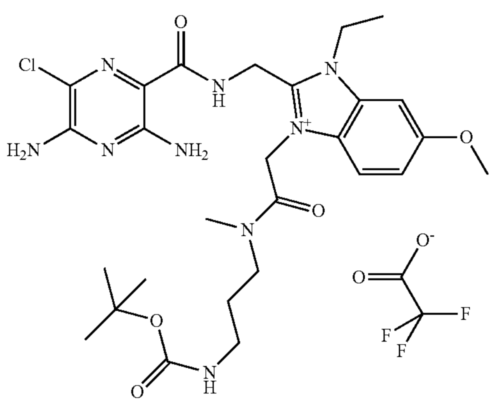 | (3-methylamino-propyl)-carbamic acid tert-butyl ester | 604 | 0.84 | B |
| 3.19 | 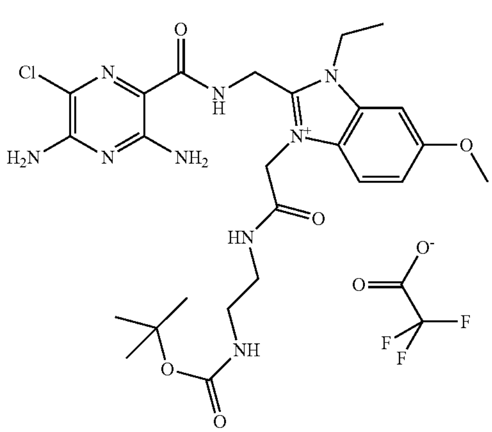 [SMILES: CCn1c(CNC(=O)c2nc(Cl)c(N)nc2N)[n+](CC(=O)NCCNC(=O)OC(C)(C)C)c2ccc(OC)cc21 ; O=C([O-])C(F)(F)F] | (2-amino-ethyl)-carbamic acid tert-butyl ester | 576 | 0.84 | B |

| Example No. | Structure | Amine applied | M+ | RT (min) | HPLC Method |
|---|---|---|---|---|---|
| 3.20 | 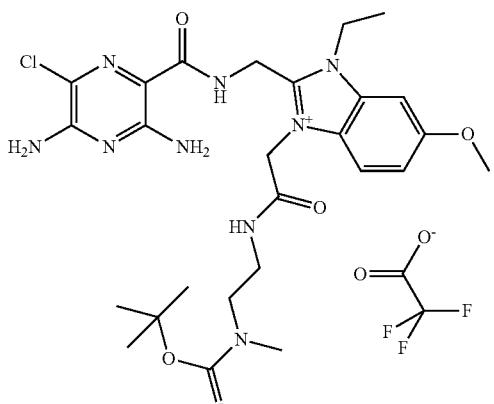 | methyl-(2-amino-ethyl)carbamic acid tert-butyl ester | 590 | 0.85 | B |
| 3.21 | 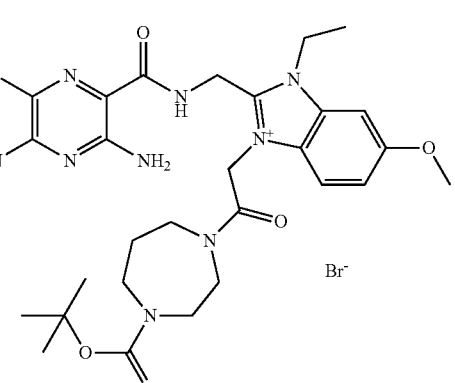 | [1,4]Diaz-epane-1-carboxylic acid tert-butyl ester | 616 | 0.85 | B |
| 3.22 | 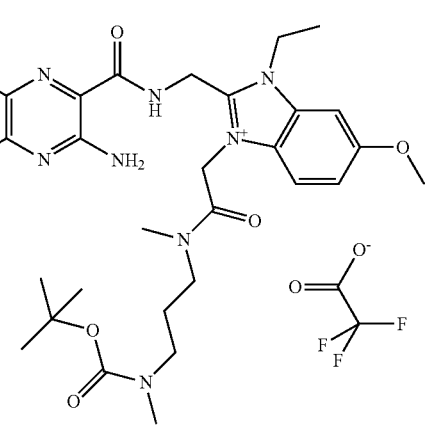 | methyl-(3-methylamino-propyl)-carbamic acid tert-butyl ester | 618 | 0.87 | B |

| Example No. | Structure | Amine applied | M+ | RT (min) | HPLC Method |
|---|---|---|---|---|---|
| 3.23 | 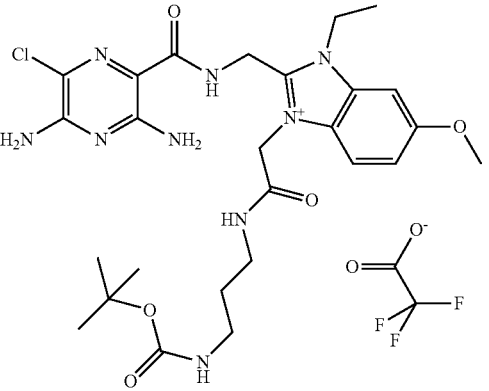 [SMILES: CCn1c(CNC(=O)c2nc(Cl)c(N)nc2N)[n+](CC(=O)NCCCNC(=O)OC(C)(C)C)c2ccc(OC)cc21 ; O=C([O-])C(F)(F)F] | (3-amino-propyl)-carbamic acid tert-butyl ester | 590 | 0.83 | B |
| 3.24 | 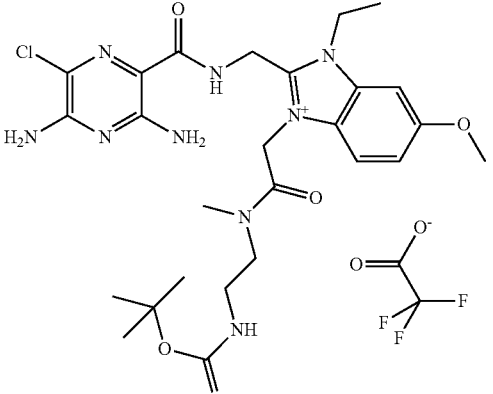 | (2-methylamino-ethyl)-carbamic acid tert-butyl ester | 590 | 0.83 | B |

Example 4.01

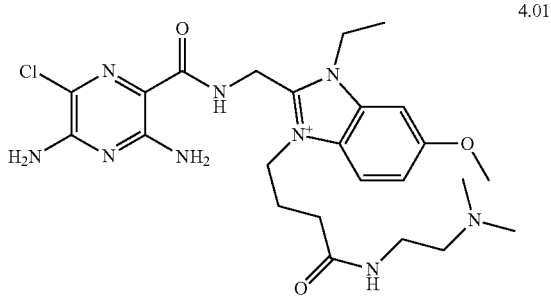

4.01

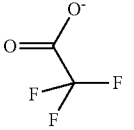

The compound is prepared from intermediate XIV.2 and 2-(dimethylamino)ethylamine according to the procedure described for example 3.01.

$C_{24}H_{35}ClN_9O_3 \times C_2F_3O_2 \times C_2HF_3O_2$ ESI Mass spectrum: m/z=532 [M]+

HPLC analytics: RT=0.67 min (HPLC method B)

Example 5.01

5.01

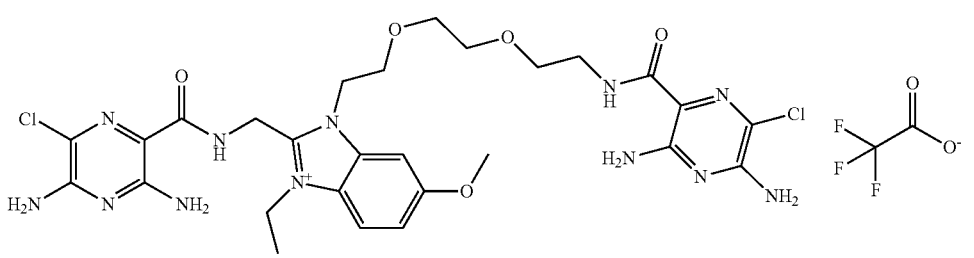

The compound is prepared from example 6.02 and intermediate A.1 according to the procedure described for example 1.01.

$C_{27}H_{35}Cl_2N_{12}O_5 \times C_2F_3O_2$ ESI Mass spectrum: m/z=677 [M]+

HPLC analytics: RT=0.40 min (HPLC method K)

Example 6.01

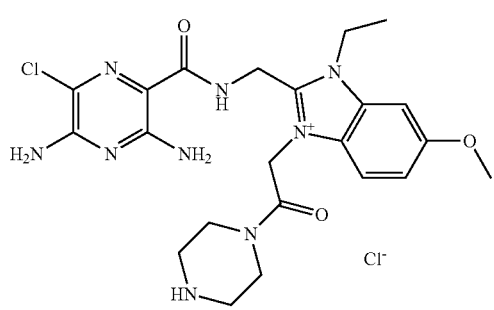

6.01

A mixture of example 3.08 (50.0 mg; 0.073 mmol) and HCl (1 mol/l in methanol; 5.0 ml; 5.0 mmol) is to stirred at r.t. for 30 min, then evaporated. The residue is triturated diethyl ether and the solid is filtered off and dried in vacuo.

$C_{22}H_{29}ClN_9O_3 \times HCl \times Cl$ ESI Mass spectrum: m/z=502 [M]+

HPLC analytics: RT=0.66 min (HPLC method B)

The following example compounds are prepared accordingly from the respective BOC compound as indicated. Depending upon conditions applied, the syntheses may yield a chloride salt, a TFA salt or other salt forms.

| Example Nr. | Structure | BOC compound applied | M+ | RT (min) | HPLC Method |
|---|---|---|---|---|---|
| 6.02 | 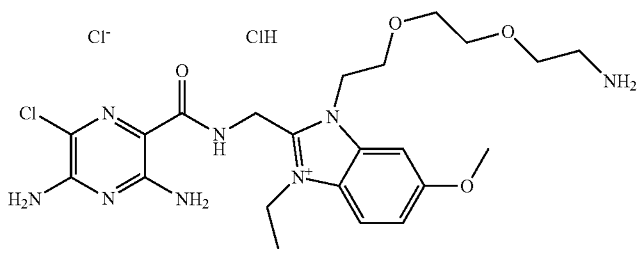 [SMILES: CC[n+]1c(CNC(=O)c2nc(Cl)c(N)nc2N)n(CCOCCOCCN)c2cc(OC)ccc21 ; [Cl-] ; Cl] | 1.01 | 507 | 0.67 | B |
| 6.03 | 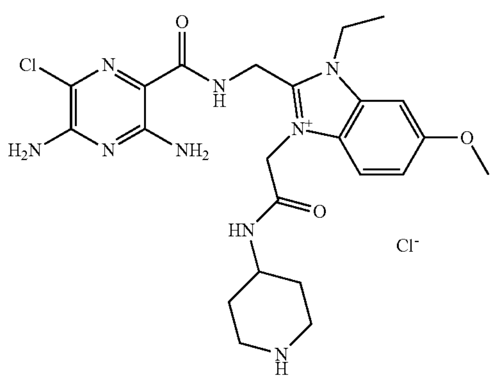 [SMILES: CCn1c(CNC(=O)c2nc(Cl)c(N)nc2N)[n+](CC(=O)NC2CCNCC2)c2ccc(OC)cc21 ; [Cl-]] | 3.12 | 516 | 0.67 | B |
| 6.04 | 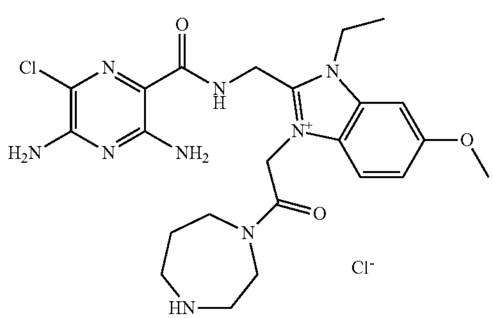 [SMILES: CCn1c(CNC(=O)c2nc(Cl)c(N)nc2N)[n+](CC(=O)N2CCCNCC2)c2ccc(OC)cc21 ; [Cl-]] | 3.21 | 516 | 0.65 | B |

-continued
| Example Nr. | Structure | BOC compound applied | M+ | RT (min) | HPLC Method |
|---|---|---|---|---|---|
| 6.05 | 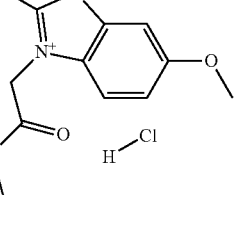 | 3.24 | 490 | 0.64 | B |
| 6.06 | 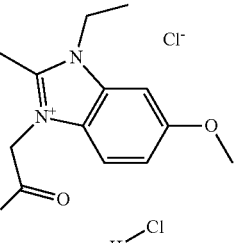 | 3.16 | 504 | 0.65 | B |
| 6.07 | 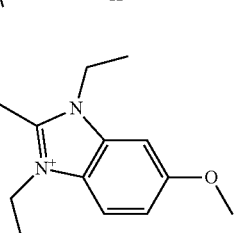 | 3.17 | 504 | 0.65 | B |
| 6.08 | 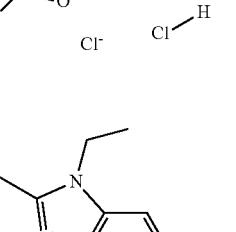 | 3.22 | 518 | 0.66 | B |
| 6.09 | 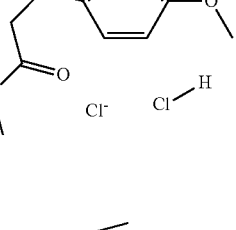 | 3.18 | 504 | 0.65 | B |

-continued

| Example Nr. | Structure | BOC compound applied | M+ | RT (min) | HPLC Method |
|---|---|---|---|---|---|
| 6.10 | 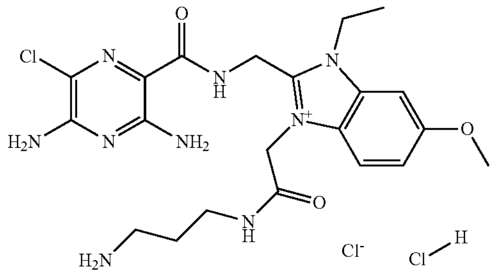 [SMILES: CCn1c(CNC(=O)c2nc(Cl)c(N)nc2N)[n+](CC(=O)NCCCN)c2ccc(OC)cc21 ; [Cl-] ; Cl] | 3.23 | 490 | 0.65 | B |
| 6.11 | 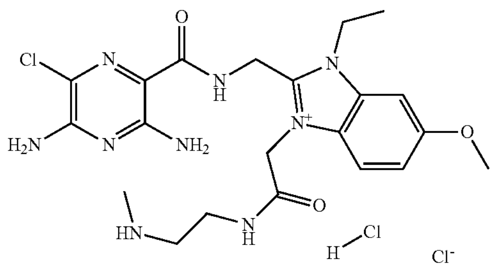 [SMILES: CCn1c(CNC(=O)c2nc(Cl)c(N)nc2N)[n+](CC(=O)NCCNC)c2ccc(OC)cc21 ; Cl ; [Cl-]] | 3.2 | 490 | 0.65 | B |
| 6.12 | 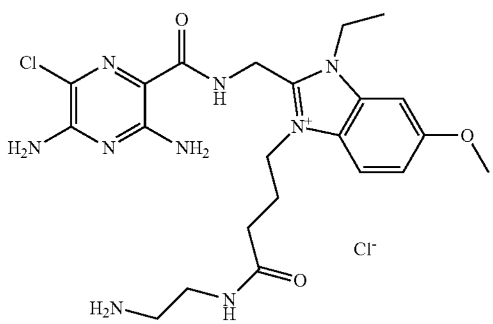 [SMILES: CCn1c(CNC(=O)c2nc(Cl)c(N)nc2N)[n+](CCCC(=O)NCCN)c2ccc(OC)cc21 ; [Cl-]] | X1.5 | 504 | 0.67 | B |
| 6.13 | 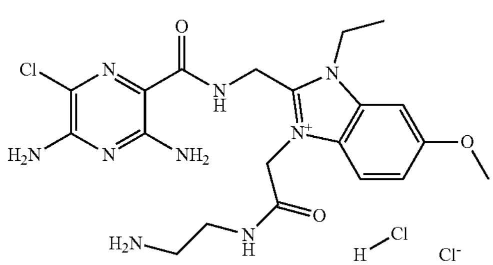 [SMILES: CCn1c(CNC(=O)c2nc(Cl)c(N)nc2N)[n+](CC(=O)NCCN)c2ccc(OC)cc21 ; Cl ; [Cl-]] | 3.19 | 476 | 0.65 | B |

Example 7.01

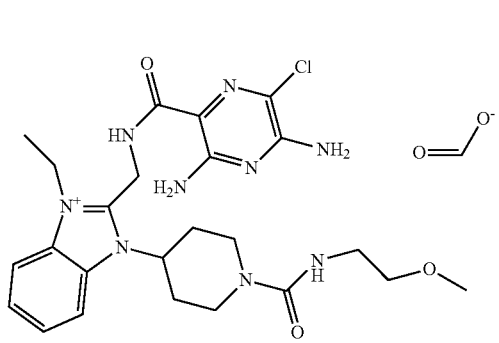

A mixture of the benzimidazole intermediate XI.3 (80.0 mg; 0.143 mmol), Iodoethane (116 µl; 1.43 mmol) and ACN (2.5 ml) is heated to 120° C. for 2 h (closed vessel; microwave irradiation). The mixture is evaporated to dryness and the crude product is purified by RP-HPLC (modifier: formic acid).

$C_{24}H_{33}ClN_9O_3 \times CHO_2$ ESI Mass spectrum: m/z=530 [M]+

HPLC analytics: RT=3.34 min (HPLC method C)

Example 8.01

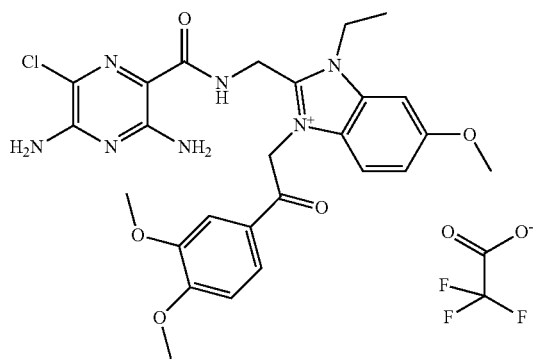

A mixture of intermediate XI.1 (45.0 mg; 0.120 mmol), triethylalmine (16.7 µl; 0.120 mmol), di-tertbutyl-dicarbonate (39.2 mg; 0.180 mmol) and ACN (3.0 ml) is stirred at r.t. for 2 min. the alkylating agent 2-Bromo-1-(3,4-dimethoxyphenyl)-ethanone (310 mg; 1.20 mmol) is added and the mixture is stirred at 80° C. for 3 h, then evaporated. The crude product is purified by RP-HPLC (modifier: TFA).

$C_{26}H_{29}ClN_7O_5 \times C_2F_3O_2$ ESI Mass spectrum: m/z=554 [M]+

HPLC analytics: RT=0.79 min (HPLC method B)

Example 9.01

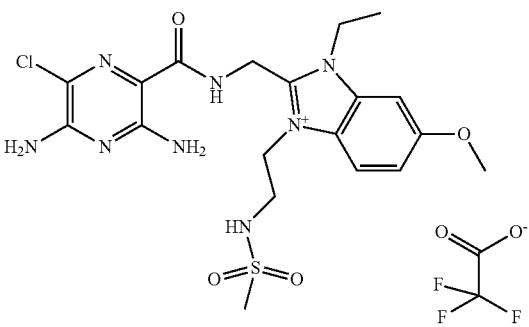

The compound is prepared from intermediate XI.1 and the alkylating agent N-(2-bromoethyl)methanesulfonamide according to the procedure described for example 8.01 (reaction at 120° C. for 2 h).

$C_{19}H_{26}ClN_8O_4S \times C_2F_3O_2$ ESI Mass spectrum: m/z=497 [M]+

HPLC analytics: RT=0.73 min (HPLC method B)

Example 10.01

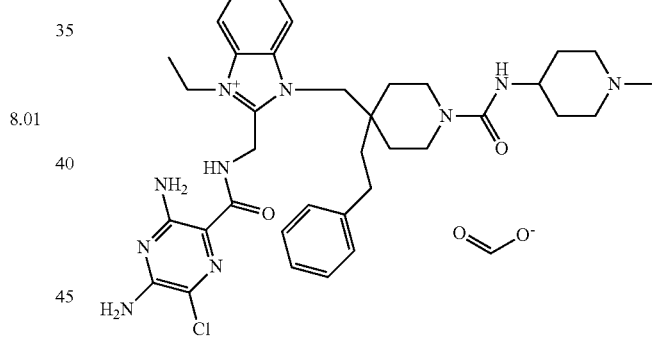

A mixture of 1,1'-carbonyldi(1,2,4-triazole) (51.9 mg; 0.316 mmol), 4-aminopiperidine (32.1 µl: 0.253 mmol) and THF (2.5 ml) is stirred at r.t. for 40 min. A mixture of intermediate III.1 (150 mg; 0.211 mmol), THF (2.5 ml) and triethylamine (73.3 µl: 0.527 mmol) is added ant the mixture is heated to 90° C. for 3 h (closed vessel; microwave heating). The mixture is evaporated to dryness and the crude product is purified by RP-HPLC (modifier: formic acid).

$C_{36}H_{48}ClN_{10}O_2 \times CHO_2$ ESI Mass spectrum: m/z=687 [M]+

HPLC analytics: RT=3.72 min (HPLC method C)

Analytical Methods and Preparative Chromatography

As a rule, $^1$H-NMR and mass spectra have been obtained for the compounds prepared. Mass peaks given (e.g. (M+H)+, (M+HCOO)−) refer to monoisotopic molecular weight. $R_f$ values from TLC are determined using ready-made silica gel 60 TLC plates $F_{254}$ (E. Merck, Darmstadt, Item no. 1.05714) without chamber saturation or using ready-made aluminium oxide 60 $F_{254}$ TLC plates (E. Merck, Darmstadt, Item no. 1.05713) without chamber saturation. The ratios given for the eluents relate to units by volume of the solvent in question. The units by volume for $NH_3$ relate to a concentrated solution of $NH_3$ in water. For silica gel chromatographic purifications, silica gel from Millipore (MATREX™, 35-70 my) is used.

Preparative Thin Layer Chromatography (TLC):

Preparative TLC plates from Merck (PLC Silica gel 60 $F_{254+366}$, 2 mm) are used. Product containing bands are scraped off and the resulting product-on-silica powder is extracted with DCM, methanol or a mixture thereof (depending on product solubility). Silica is filtered off and the filtrate is evaporated to dryness to to yield the purified compound.

Preparative HPLC:

Stationary phase (unless stated otherwise): XBridge C18; 10 μm or SunFire C18; 10 μm (both from waters, www.waters.com)

Analytical HPLC/MS Methods

The HPLC retention times given are measured under the following parameters.

| HPLC method A | | | | |
|---|---|---|---|---|
| Column: | SunFire C18, 2.1 × 30 mm, 2.5 μm (Waters) | | | |
| Gradient time [min] | % Sol [H2O, 0.1% TFA] | % Sol [ACN] | Flow [ml/min] | Temp [° C.] |
| 0.00 | 99 | 1 | 1.5 | 60 |
| 0.02 | 99 | 1 | 1.5 | 60 |
| 1.00 | 0 | 100 | 1.5 | 60 |
| 1.10 | 0 | 100 | 1.5 | 60 |

| HPLC method B | | | | |
|---|---|---|---|---|
| Column: | SunFire, 3 × 30 mm, 2.5 μm (Waters) | | | |
| Gradient time [min] | % Sol [H2O, 0.1% TFA] | % Sol [ACN] | Flow [ml/min] | Temp [° C.] |
| 0.00 | 97 | 3 | 2.2 | 60 |
| 0.20 | 97 | 3 | 2.2 | 60 |
| 1.20 | 0 | 100 | 2.2 | 60 |
| 1.25 | 0 | 100 | 3 | 60 |
| 1.40 | 0 | 100 | 3 | 60 |

| HPLC method C | |
|---|---|
| Column: | Atlantis dC18 5 μm 4.6 × 50 mm, Temp 35° C. |
| Mobile phase: | A = H2O 90% + 10% CH3CN + CF3COOH 0.05% |
| | B = CH3CN 90% + 10% H2O |

| Time in min | % A | % B | flow rate in ml/min |
|---|---|---|---|
| 0.00 | 100 | 0 | 1.3 |
| 0.70 | 100 | 0 | 1.3 |
| 4.5 | 0 | 100 | 1.3 |
| 5.80 | 0 | 100 | 1.3 |
| 6.00 | 100 | 0 | 1.3 |

| HPLC method D | | | | |
|---|---|---|---|---|
| Column: | Sunfire C18_3.0 × 30 mm, 2.5 μm (Waters) | | | |
| Gradient Time [min] | % Sol [H2O 0.1% TFA] | % Sol [Acetonitrile] | Flow [ml/min] | Temp [° C.] |
| 0.0 | 99.0 | 1.0 | 2.0 | 60.0 |
| 0.9 | 0.0 | 100.0 | 2.0 | 60.0 |
| 1.1 | 0.0 | 100.0 | 2.0 | 60.0 |

| HPLC method E | | | | |
|---|---|---|---|---|
| Column: | Sunfire C18_3.0 × 30 mm, 2.5 μm (Waters) | | | |
| Gradient Time [min] | % Sol [H2O 0.1% TFA] | % Sol [Acetonitrile] | Flow [ml/min] | Temp [° C.] |
| 0.0 | 98.0 | 2.0 | 2.0 | 60.0 |
| 1.2 | 0.0 | 100.0 | 2.0 | 60.0 |
| 1.4 | 0.0 | 100.0 | 2.0 | 60.0 |

| HPLC method F | | | |
|---|---|---|---|
| Column: | BEH C18 1.7 μm 2.1 × 50 mm, Temp 35° C. | | |
| Mobile phase: | A = H2O 90% + CH3CN 10% + NH4COOH 5 mM | | |
| | B = CH3CN 90% + H2O 10% | | |

| Time in min | % A | % B | flow rate in mL/min |
|---|---|---|---|
| 0.00 | 100 | 0 | 0.70 |
| 1.20 | 0 | 100 | 0.70 |
| 1.45 | 0 | 100 | 0.70 |
| 1.55 | 100 | 0 | 0.70 |
| 1.75 | 100 | 0 | 0.70 |

| HPLC method K | | | | |
|---|---|---|---|---|
| Column: | SunFire C18, 2.1 × 50 mm, 2.5 μm (Waters) | | | |
| Gradient time [min] | % Sol [H2O, 0.1% TFA] | % Sol [ACN, 0.08% TFA] | Flow [ml/min] | Temp [° C.] |
| 0.00 | 95 | 5 | 1.5 | 60 |
| 0.75 | 0 | 100 | 1.5 | 60 |
| 0.85 | 0 | 100 | 1.5 | 60 |

The following abbreviations are used above and hereinafter:

ACN Acetonitrile
BOC tert-Butoxycarbonyl
Cbz Carbobenzyloxy
CH Cyclohexane
DCM Dichloromethane
DIPEA Diisopropyl-ethylamine
DMAP 4-Dimethylaminopyridine
DMF N,N-Dimethylformamide
DPPF 1,1'-Bis(diphenylphosphino)ferrocene
EDC 1-Ethyl-3-(3-dimethylaminopropyl)carbodiimide hydrochloride
EE Ethyl acetate
Eq. Molar equivalent ESI Electrospray ionization
h hour
HATU O-(7-Azabenzotriazol-1-yl)-N,N,N',N'-tetramethyl-uronium hexafluorophosphate
HCl Hydrochloric acid
KOH Potassium hydroxide
l liter
LiHMDS Lithium bis(trimethylsilyl)amide
M mol/l
Min minutes
Mp melting point
NaOH Sodium hydroxide
n.d. not determined
NMP N-Methylpyrrolidone
Pd/C palladium on charcoal
r.t. ambient temperature (about 20° C.)
RT retention time
TBME Methyl tert-butyl ether
TBTU 2-(1H-Benzotriazol-1-yl)-1,1,3,3-tetramethyluro-nium-tetrafluoroborate
TEA Triethylamine
TFA Trifluoroacetic acid
THF Tetrahydrofurane
TLC Thin Layer Chromatography
TMS Trimethylsilyl
Pharmacological Test Method The $IC_{50}$ values of the example compounds given above were determined in the Ussing Chamber assay.

Ussing Chamber: Mouse kidney M-1 cells were cultivated in DMEM containing 5% FCS and 5 µM dexamethasone for 10 to 12 days on polyester transwell filters. Filters were inserted into a teflon-coated well-plate which fit into the ussing chamber system. Prior to measurement the medium of M-1 cells was replaced with Caco-2 transport buffer (Invitrogen, Germany). During measurements, the Ussing chamber temperature was kept at 37° C. Short circuit currents (I_sc) were measured in the voltage-clamp mode with the software package Lab View for data acquisition and analysis. The transepithelial electrical resistance (TEER) was determined by the application of voltage steps of ±5 mV every 5 sec. Compounds were administered at a final concentration of 3 µM or at increasing concentrations (1-3-10 µM) to the apical solution. At the end of each experiment the amiloride sensitive I_SC was measured by adding 3 µM amiloride to the apical compartment. Results are expressed as inhibition in percent of the amiloride effect or as $IC_{50}$.

With the example compounds given above, the following $IC_{50}$ values were determined in the Ussing Chamber assay:

| Example | | | | | | | | | | | |
|---|---|---|---|---|---|---|---|---|---|---|---|
| 1.01 | 1.02 | 1.03 | 1.04 | 1.05 | 2.01 | 3.01 | 3.02 | 3.03 | 3.04 | 3.05 | 3.06 |
| $IC_{50}$ [nM] 3 | 2 | 8 | 2 | 0.4 | 2 | 10 | 5 | 4 | 3 | 12 | 8 |

| Example | | | | | | | | | | | |
|---|---|---|---|---|---|---|---|---|---|---|---|
| 3.07 | 3.08 | 3.09 | 3.10 | 3.11 | 3.12 | 3.13 | 3.14 | 3.15 | 3.17 | 3.21 | 4.01 |
| $IC_{50}$ [nM] 39 | 4 | 33 | 1 | 110 | 12 | 7 | 2 | 20 | 4 | 28 | 1 |

| Example | | | | | | | | | |
|---|---|---|---|---|---|---|---|---|---|
| 5.01 | 6.01 | 6.02 | 6.03 | 6.04 | 7.01 | 8.01 | 9.01 | 10.01 |
| $IC_{50}$ [nM] 4 | 47 | 4 | 17 | 63 | 1 | 13 | 0.4 | 2 |

Permeability in CALU-3 Cells:

Permeability measurements across polarized, confluent CALU-3 cell monolayers grown on permeable filter supports are used to provide information on the potential of a compound to pass the lung epithelium. Apparent permeability coefficients (Papp) of the compounds across the CALU-3 cell monolayers are measured (pH 7.4, 37° C.) in apical-to-basal (AB) and basal-to-apical (BA) transport direction. AB permeability (Papp, AB) represents drug absorption from the lung lumen into the blood and BA permeability (Papp, BA) drug transport from the blood into the lung lumen mainly via passive permeability since Calu-3 cells as well as lung epithelial cells do not express efflux transporters like P-gp, while uptake transporters may be expressed.

CALU-3 cells ($1-2 \times 10^5$ cells/l $cm^2$ area) are seeded on filter inserts (Costar transwell polycarbonate filters, 0.4 µm pore size) and cultured (for 10-12 days DMEM) until tight monolayers are formed. Compounds of interest are dissolved in appropriate solvent (DMSO, 10 mM stock solution). Stock solutions are diluted with HTP-4 buffer (128.13 mM NaCl, 5.36 mM KCl, 1 mM MgSO4, 1.8 mM CaCl2, 4.17 mM NaHCO3, 1.19 mM Na2HPO4×7H2O, 0.41 mM NaH2PO4×H2O, 15 mM HEPES, 20 mM glucose, 0.25% BSA, pH 7.4) to prepare the transport solutions (10 µM compound, final DMSO <=0.5%). The transport solution (TL) is applied to the apical or basolateral donor side for measuring A-B or B-A permeability (3 filter replicates), respectively. The receiver side contains the same buffer as the donor side. After 30 min of accommodation, samples are collected at the start t0=0 min and at the end of the experiment tn=90 min from the donor and at 0, 30, 60, and 90 min also from the receiver chamber. Volume removed is replenwashed by HTP-4 buffer. The compound concentration in the samples is measured by HPLC-MS/MS or scintillation counting. The permeability coefficient (Papp) and efflux ratio are calculated according to: Papp [cm/s]=(concentration receiver [nM]*volume receiver [mL]/time interval [sec])*(1/filter area)*(1/donor concentration [nM]).

With example compounds given above, the following permeability values were determined in the CALU-3 cells assay:

| | Example | | | | | | | | |
|---|---|---|---|---|---|---|---|---|---|
| | 1.03 | 3.02 | 3.06 | 3.08 | 3.12 | 3.13 | 6.01 | 7.01 | 8.01 |
| Papp, AB [$10^{-6}$ cm/s] | 0.1 | 0.06 | 0.1 | 0.1 | 0.09 | 0.07 | 0.3 | 0.07 | 0.3 |
| Papp, BA [$10^{-6}$ cm/s] | 0.07 | 0.2 | 0.03 | 0.08 | 0.3 | 0.2 | 0.2 | 0.2 | 0.2 |

Indications

As has been found, the compounds of formula (I) are characterised by their wide range of applications in the therapeutic field. Particular mention should be made of those applications for which the compounds according to the invention of formula (I) are preferably suited on account of their pharmaceutical efficacy as ENaC inhibitors. Examples include respiratory diseases or complaints, or allergic diseases of the airways.

Particular mention should be made of the prevention and treatment of diseases of the airways and of the lung which are accompanied by increased mucus production, inflammations and/or obstructive diseases of the airways. Examples include acute, allergic or chronic bronchitis, chronic obstructive bronchitis (COPD), coughing, pulmonary emphysema, allergic or non-allergic rhinitis or sinusitis, chronic rhinitis or sinusitis, asthma, alveolitis, Farmer's disease, hyperreactive airways, infectious bronchitis or pneumonitis, paediatric asthma, bronchiectases, pulmonary fibrosis, ARDS (acute adult respiratory distress syndrome), bronchial oedema, pulmonary oedema, bronchitis, pneumonia or interstitial pneumonia triggered by various causes, such as aspiration, inhalation of toxic gases, or bronchitis, pneumonia or interstitial pneumonia as a result of heart failure, irradiation, chemotherapy, cystic fibrosis or mucoviscidosis, or alpha1-antitrypsin deficiency.

Particularly preferably the present invention relates to the use of compounds of formula (I) for preparing a pharmaceutical composition for the treatment of inflammatory or obstructive diseases of the upper and lower respiratory tract including the lungs, such as for example allergic rhinitis, chronic rhinitis, bronchiectasis, cystic fibrosis, COPD, chronic bronchitis, chronic sinusitis and asthma.

It is most preferable to use the compounds of formula (I) for the treatment of inflammatory and obstructive diseases such as COPD, chronic bronchitis, chronic sinusitis, asthma, cystic fibrosis, particularly COPD, chronic bronchitis, asthma and cystic fibrosis.

The actual pharmaceutically effective amount or therapeutic dosage will of course depend on factors known by those skilled in the art such as age and weight of the patient, route of administration and severity of disease. In any case the combination will be administered at dosages and in a manner which allows a pharmaceutically effective amount to be delivered based upon patient's unique condition.

Combinations

The compounds of formula (I) may be used on their own or in conjunction with other active substances of formula (I) according to the invention. If desired the compounds of formula (I) may also be used in combination with other pharmacologically active substances.

Therefore the invention further relates to medicament combinations which preferably contain, besides one or more compounds of formula (I) or a salt thereof, as further active substances, one or more compounds selected from among the categories of further ENaC inhibitors, betamimetics, anticholinergics, corticosteroids, PDE4-inhibitors, LTD4-antagonists, EGFR-inhibitors, dopamine agonists, H1-antihistamines, PAF-antagonists, MAP-kinase inhibitors, MPR4-Inhibitors, iNOS-Inhibitors, SYK-Inhibitors, corrections of the cystic fibrosis transmembrane regulator (CFTR) and CFTR potentiators, or double or triple combinations thereof.

Formulations

Suitable forms for administration are for example inhalable powders or aerosols. The content of the pharmaceutically effective compound(s) in each case should be in the range from 0.2 to 50 wt %, preferably 5 to 25 wt % of the total composition, i.e. in amounts which are sufficient to achieve the dosage range specified hereinafter.

Administered by inhalation the active substance combination may be given as a powder, as an aqueous or aqueous-ethanolic solution or using a propellant gas formulation.

Preferably, therefore, pharmaceutical formulations are characterised in that they contain one or more compounds of formula (I) according to the preferred embodiments above.

It is also preferred if the compounds of formula (I) are administered by inhalation, particularly preferably if they are administered once or twice a day. For this purpose, the compounds of formula (I) have to be made available in forms suitable for inhalation. Inhalable preparations include inhalable powders, propellant-containing metered-dose aerosols or propellant-free inhalable solutions, which are optionally present in admixture with conventional physiologically acceptable excipients.

Within the scope of the present invention, the term propellant-free inhalable solutions also include concentrates or sterile ready-to-use inhalable solutions. The preparations which may be used according to the invention are described in more detail in the next part of the specification.

Inhalable Powders

If the active substances of formula (I) are present in admixture with physiologically acceptable excipients, the following physiologically acceptable excipients may be used to prepare the inhalable powders according to the invention: monosaccharides (e.g. glucose or arabinose), disaccharides (e.g. lactose, saccharose, maltose), oligo- and polysaccharides (e.g. dextran), polyalcohols (e.g. sorbitol, mannitol, xylitol), salts (e.g. sodium chloride, calcium carbonate) or mixtures of these excipients with one another. Preferably, mono- or disaccharides are used, while the use of lactose or glucose is preferred, particularly, but not exclusively, in the form of their hydrates. For the purposes of the invention, lactose is the particularly preferred excipient, while lactose monohydrate is most particularly preferred. Methods of preparing the inhalable powders according to the invention by grinding and micronising and by finally mixing the components together are known from the prior art.

Propellant-Containing Inhalable Aerosols

The propellant-containing inhalable aerosols which may be used according to the invention may contain a compound of formula (I) dissolved in the propellant gas or in dispersed form. The propellant gases which may be used to prepare the inhalation aerosols according to the invention are known from the prior art. Suitable propellant gases are selected from among hydrocarbons such as n-propane, n-butane or isobutane and halohydrocarbons such as preferably fluorinated derivatives of methane, ethane, propane, butane, cyclopropane or cyclobutane. The propellant gases mentioned above may be used on their own or in mixtures thereof. Particularly preferred propellant gases are fluorinated alkane derivatives selected from TG134a (1,1,1,2-tetrafluoroethane), TG227 (1,1,1,2,3,3,3-heptafluoropropane) and mixtures thereof. The propellant-driven inhalation aerosols used within the scope of the use according to the invention may also contain other ingredients such as co-solvents, stabilisers, surfactants, antioxidants, lubricants and pH adjusters. All these ingredients are known in the art.

Propellant-Free Inhalable Solutions

The compounds of formula (I) according to the invention are preferably used to prepare propellant-free inhalable solutions and inhalable suspensions. Solvents used for this purpose include aqueous or alcoholic, preferably ethanolic solutions. The solvent may be water on its own or a mixture of water and ethanol. The solutions or suspensions are adjusted to a pH of 2 to 7, preferably 2 to 5, using suitable acids. The pH may be adjusted using acids selected from inorganic or organic acids. Examples of particularly suitable inorganic acids include hydrochloric acid, hydrobromic acid, nitric acid, sulphuric acid and/or phosphoric acid. Examples of particularly suitable organic acids include ascorbic acid, citric acid, malic acid, tartaric acid, maleic acid, succinic acid, fumaric acid, acetic acid, formic acid and/or propionic acid etc. Preferred inorganic acids are hydrochloric and sulphuric acids. It is also possible to use the acids which have already formed an acid addition salt with one of the active substances. Of the organic acids, ascorbic acid, fumaric acid and citric acid are preferred. If desired, mixtures of the above acids may also be used, particularly in the case of acids which have other properties in addition to their acidifying qualities, e.g. as flavourings, antioxidants or complexing agents, such as citric acid or ascorbic acid, for example. According to the invention, it is particularly preferred to use hydrochloric acid to adjust the pH.

Co-solvents and/or other excipients may be added to the propellant-free inhalable solutions used for the purpose according to the invention. Preferred co-solvents are those which contain hydroxyl groups or other polar groups, e.g. alcohols—particularly isopropyl alcohol, glycols—particularly propyleneglycol, polyethyleneglycol, polypropyleneglycol, glycolether, glycerol, polyoxyethylene alcohols and polyoxyethylene fatty acid esters. The terms excipients and additives in this context denote any pharmacologically acceptable substance which is not an active substance but which can be formulated with the active substance or substances in the pharmacologically suitable solvent in order to improve the qualitative properties of the active substance formulation. Preferably, these substances have no pharmacological effect or, in connection with the desired therapy, no appreciable or at least no undesirable pharmacological effect. The excipients and additives include, for example, surfactants such as soya lecithin, oleic acid, sorbitan esters, such as polysorbates, polyvinylpyrrolidone, other stabilisers, complexing agents, antioxidants and/or preservatives which guarantee or prolong the shelf life of the finwashed pharmaceutical formulation, flavourings, vitamins and/or other additives known in the art. The additives also include pharmacologically acceptable salts such as sodium chloride as isotonic agents. The preferred excipients include antioxidants such as ascorbic acid, for example, provided that it has not already been used to adjust the pH, vitamin A, vitamin E, tocopherols and similar vitamins or provitamins occurring in the human body. Preservatives may be used to protect the formulation from contamination with pathogens. Suitable preservatives are those which are known in the art, particularly cetyl pyridinium chloride, benzalkonium chloride or benzoic acid or benzoates such as sodium benzoate in the concentration known from the prior art.

For the treatment forms described above, ready-to-use packs of a medicament for the treatment of respiratory complaints are provided, containing an enclosed description including for example the words respiratory disease, COPD or asthma, a compound according to the invention and one or more combination partners selected from those described above.

What we claim:

1. A compound of formula (I), or a tautomer thereof or a pharmacologically acceptable acid addition salt of the compound or the tautomer,

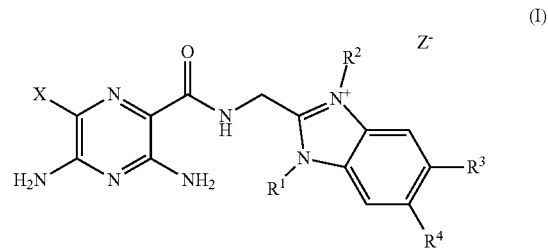

wherein
$R^3$ is H or $C_1$-$C_4$-alkoxy;
$R^4$ is H or $C_1$-$C_4$-alkoxy;
X is Cl or Br; and
$Z^-$ is chloride, bromide, iodide, hydroxide, hydrogensulfate, sulfate, nitrate, phosphate, formate, acetate, trifluoroacetate, fumarate, citrate, tartrate, oxalate, succinate, mandelate, methanesulfonate or p-toluenesulfonate;
wherein the compound of formula (I) is characterized by a topological polar surface area value (TPSA) of at least 145; and
wherein at least one of $R^1$ and $R^2$ is independently selected from a group of formula (A),

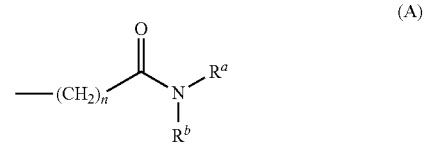

wherein
n is 1, 2 or 3, and
$R^a$ and $R^b$ are independently selected from H, $C_1$-$C_4$-alkyl,
wherein $C_1$-$C_4$-alkyl in the aforementioned moiety may carry a substituent selected from amino, $C_1$-$C_4$-alkylamino, di($C_1$-$C_4$-alkyl)amino, hydroxy, $C_1$-$C_4$-alkoxy, $C_1$-$C_4$-alkoxycarbonylamino-, and $C_1$-$C_4$-alkoxycarbonyl($C_1$-$C_4$-alkyl)amino-, or a 5- to 7-membered heterocycle containing 1 or 2 heteroatoms selected from O and N, wherein the 5- to 7-membered heterocycle may carry one substituent selected from $C_1$-$C_4$-alkyl and $C_1$-$C_4$-alkoxycarbonyl-;

or wherein $R^a$ and $R^b$ together with the nitrogen they are attached to form a 5- to 7-membered heterocycle containing 1 or 2 heteroatoms selected from O and N, wherein the 5- to 7-membered heterocyclyl may carry one substituent selected from $C_1$-$C_4$-alkyl, amino, $C_1$-$C_4$-alkylamino, di($C_1$-$C_4$-alkyl)amino, hydroxy, $C_1$-$C_4$-alkoxy, and $C_1$-$C_4$-alkoxycarbonyl-;

and/or wherein at least one of $R^1$ and $R^2$ is independently selected from a group of formula (B),

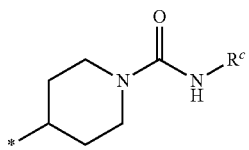
(B)

wherein $R^c$ is selected from $C_1$-$C_3$-alkyl, $C_1$-$C_2$-alkoxy-$C_2$-$C_3$-alkyl-, hydroxy-$C_2$-$C_3$-alkyl-, and amino-$C_2$-$C_3$-alkyl-, and wherein * denotes the point of attachment;

and/or wherein at least one of $R^1$ and $R^2$ is independently selected from

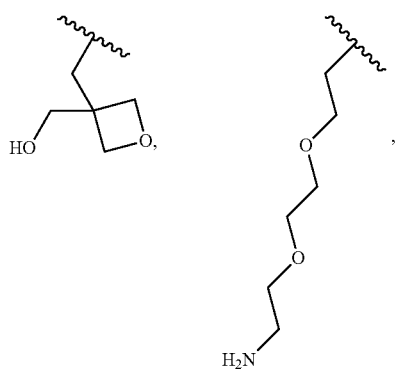

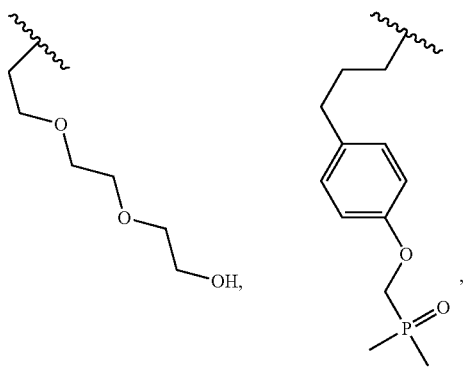

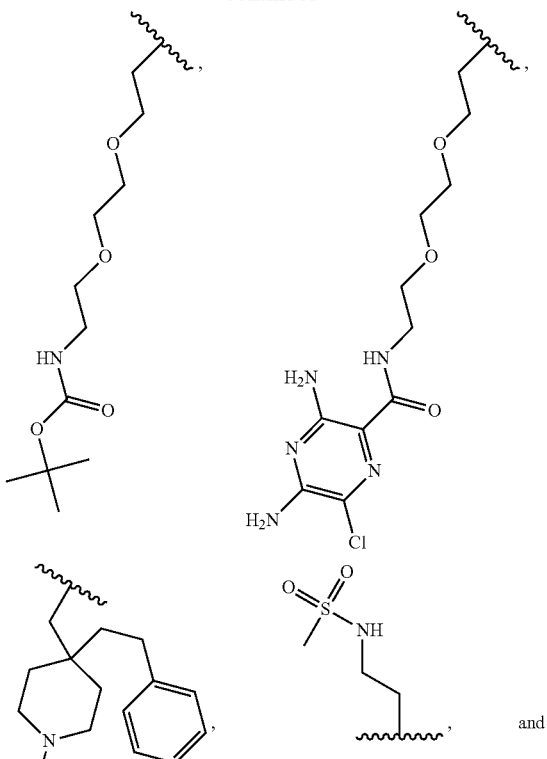

wherein denotes the point of attachment; and the remaining substituent $R^1$ or $R^2$ may additionally be selected from $C_1$-$C_3$-alkyl, ω-fluoro-$C_2$-$C_3$-alkyl, 2-propenyl, dimethylaminocarbonylmethyl, and dimethylaminocarbonylpropyl;

provided that if one of the substituents $R^1$ or $R^2$ is selected from $C_1$-$C_3$-alkyl the other substituent $R^1$ or $R^2$ is different from —($CH_2$—$CH_2$—O$)_3$H.

2. The compound of formula (I) according to claim 1, or a tautomer thereof or a pharmacologically acceptable acid addition salt of the compound or the tautomer, wherein $R^3$ is H or —OCH$_3$.

3. The compound of formula (I) according to claim 1, or a tautomer thereof or a pharmacologically acceptable acid addition salt of the compound or the tautomer, wherein $R^4$ is H or —OCH$_3$.

4. The compound of formula (I) according to claim 1, or a tautomer thereof or a pharmacologically acceptable acid addition salt of the compound or the tautomer, wherein $Z^-$ is chloride, bromide, formate, or trifluoroacetate.

5. The compound of formula (I) according to claim 1, or a tautomer thereof or a pharmacologically acceptable acid addition salt of the compound or the tautomer, wherein at least one of $R^1$ and $R^2$ is independently selected from the group of formula (A).

6. The compound of formula (I) according to claim 5, or a tautomer thereof or a pharmacologically acceptable acid addition salt of the compound or the tautomer, wherein n is 1.

7. The compound of formula (I) according to claim 6, or a tautomer thereof or a pharmacologically acceptable acid addition salt of the compound or the tautomer, wherein the group of formula (A) is selected from

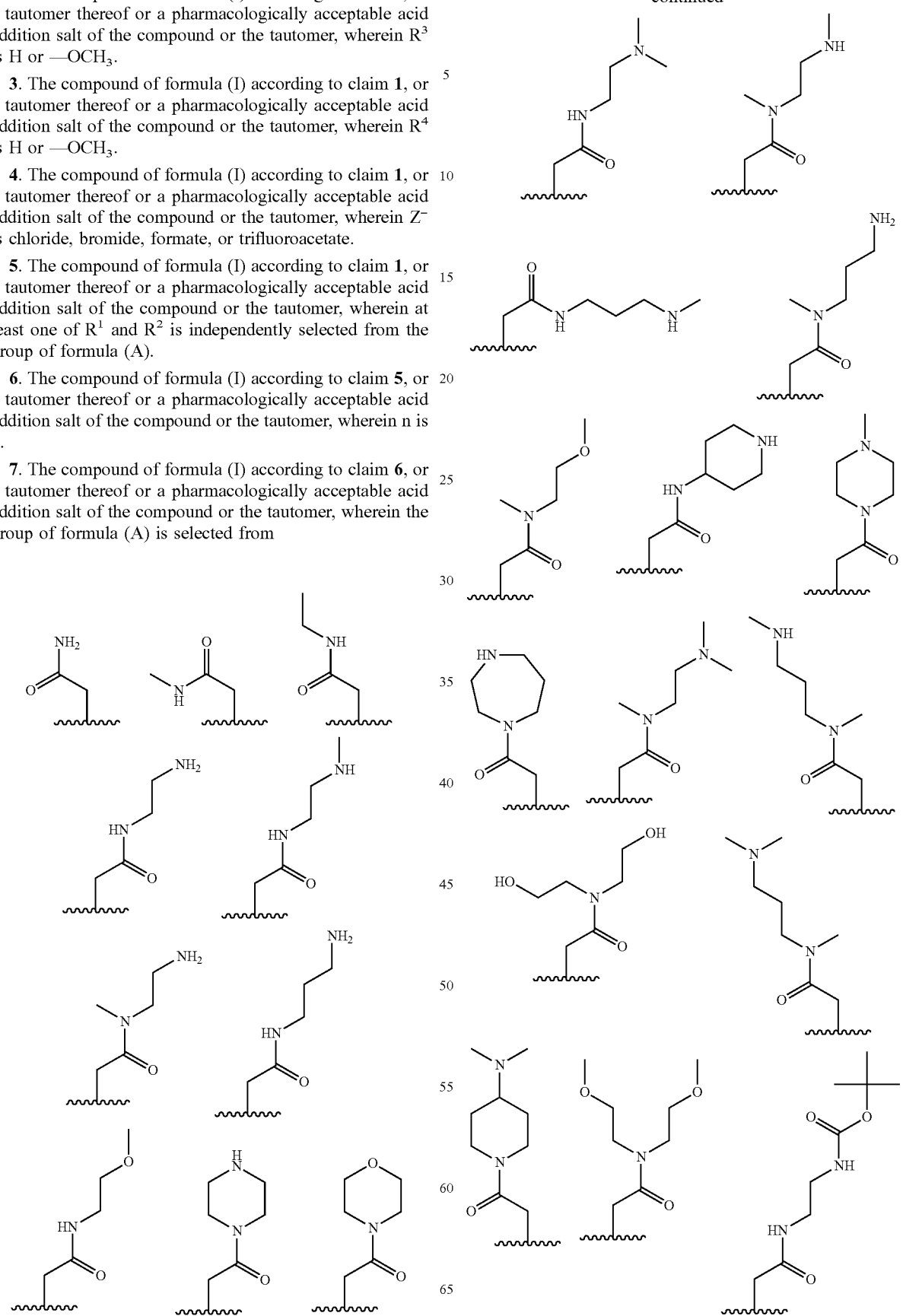

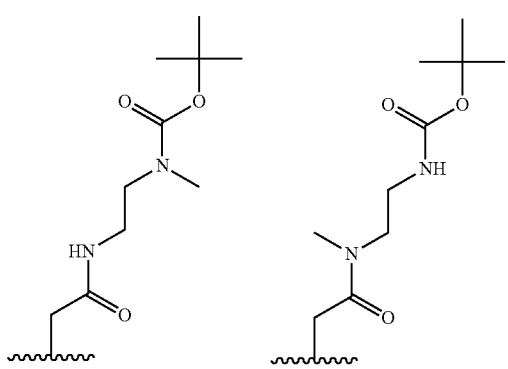
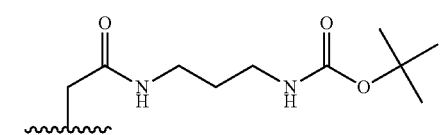
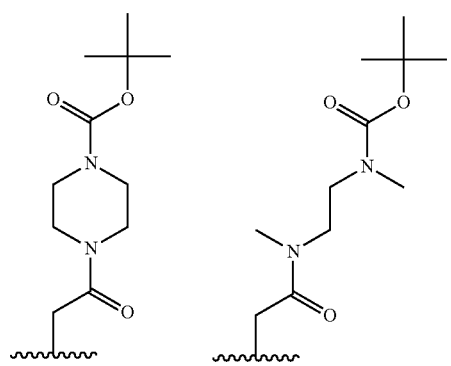
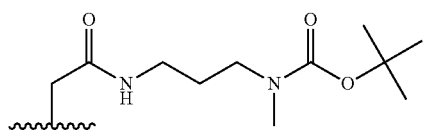
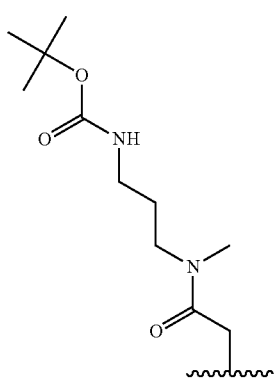

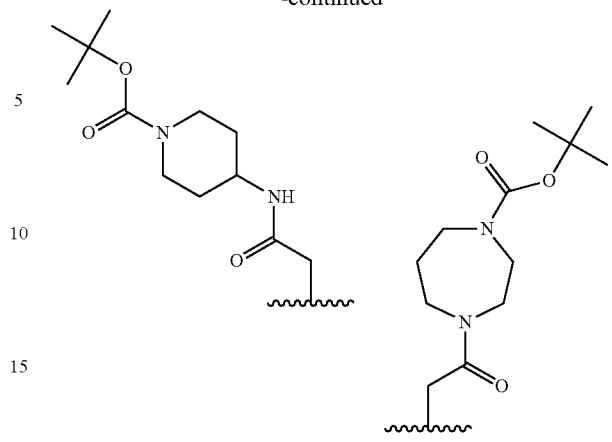

8. The compound of formula (I) according to claim 5, or a tautomer thereof or a pharmacologically acceptable acid addition salt of the compound or the tautomer, wherein n is 3.

9. The compound of formula (I) according to claim 8, or a tautomer thereof or a pharmacologically acceptable acid addition salt of the compound or the tautomer, wherein the group of formula (A) is selected from

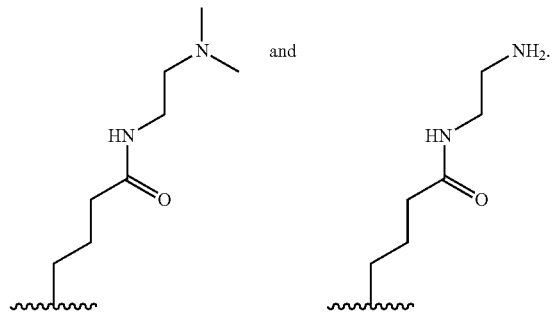 [SMILES: *CCCC(=O)NCCN(C)C ; "and" ; *CCCC(=O)NCCN]

10. The compound of formula (I) according to claim 1, or a tautomer thereof or a pharmacologically acceptable acid addition salt of the compound or the tautomer, wherein at least one of $R^1$ and $R^2$ is independently selected from a group of formula (B).

11. The compound of formula (I) according to claim 10, or a tautomer thereof or a pharmacologically acceptable acid addition salt of the compound or the tautomer, wherein the group of formula (B) is

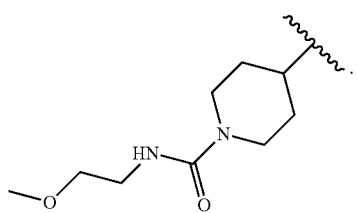 [SMILES: *C1CCN(C(=O)NCCOC)CC1]

12. The compound of formula (I) according to claim 1, or a tautomer thereof or a pharmacologically acceptable acid addition salt of the compound or the tautomer, wherein the remaining substituent $R^1$ or $R^2$ is selected from ethyl, 2-fluoroethyl, 2-propenyl, and dimethylaminocarbonylmethyl.

13. A method of treating a disease comprising administering an effective amount of a compound according to claim 1 or a tautomer thereof or a pharmacologically acceptable acid addition salt of the compound or the tautomer, wherein the disease is selected from the group consisting of a respiratory disease, a respiratory complaint, and an allergic disease of the airways.

14. A method of treating a disease comprising administering an effective amount of a compound according to claim 1 a tautomer thereof or a pharmacologically acceptable acid addition salt of the compound or the tautomer, wherein the disease is selected from the group consisting of chronic bronchitis, acute bronchitis, bronchitis caused by bacterial or viral infection or fungi or helminths, allergic bronchitis, toxic bronchitis, chronic obstructive bronchitis (COPD), asthma (intrinsic or allergic), pediatric asthma, bronchiectasis, allergic alveolitis, allergic or non-allergic rhinitis, chronic sinusitis, cystic fibrosis, mucoviscidosis, alpha-1-antitrypsin deficiency, cough, pulmonary emphysema, interstitial lung diseases, alveolitis, hyperreactive airways, nasal polyps, pulmonary oedema, pneumonitis of different origins, and dry eyes.

15. A pharmaceutical composition comprising a compound of claim 1 or a tautomer thereof or a pharmacologically acceptable acid addition salt of the compound or the tautomer and a pharmaceutically acceptable carrier.

16. A pharmaceutical composition comprising a compound of claim 1, or a tautomer thereof or a pharmacologically acceptable acid addition salt of the compound or the tautomer, and one or more compounds selected from among the group consisting of an ENaC inhibitor, a betamimetic, an anticholinergic, a corticosteroid, an PDE4-inhibitor, an LTD4-antagonist, an EGFR-inhibitor, a dopamine agonist, an H1 antihistamine, a PAF-antagonist, a MAP-kinase inhibitor, an MPR4-Inhibitor, an iNOS-Inhibitor, a SYK-Inhibitor, a cystic fibrosis transmembrane regulator (CFTR) potentiator, and double or triple combinations thereof.

* * * * *